United States Patent
Nguyen et al.

(10) Patent No.: US 9,439,772 B2
(45) Date of Patent: Sep. 13, 2016

(54) MULTI-LOBE ARTIFICIAL SPINE JOINT

(71) Applicant: Dimicron, Inc., Orem, UT (US)

(72) Inventors: Bao-Khang Ngoc Nguyen, Holladay, UT (US); David P Harding, Provo, UT (US)

(73) Assignee: DIMICRON, INC., Orem, UT (US)

( * ) Notice: Subject to any disclaimer, the term of this patent is extended or adjusted under 35 U.S.C. 154(b) by 0 days.

(21) Appl. No.: 14/788,470

(22) Filed: Jun. 30, 2015

(65) Prior Publication Data
US 2015/0374505 A1  Dec. 31, 2015

Related U.S. Application Data

(63) Continuation of application No. 14/099,945, filed on Dec. 7, 2013, now Pat. No. 9,078,763, which is a continuation of application No. 13/445,833, filed on Apr. 12, 2012, now Pat. No. 8,603,169, which is a continuation of application No. 12/028,740, filed on Feb. 8, 2008, now Pat. No. 8,163,023.

(60) Provisional application No. 60/914,469, filed on Apr. 27, 2007, provisional application No. 60/889,217, filed on Feb. 9, 2007.

(51) Int. Cl.
*A61F 2/44* (2006.01)
*A61F 2/30* (2006.01)

(52) U.S. Cl.
CPC .............. *A61F 2/442* (2013.01); *A61F 2/4425* (2013.01); *A61F 2/30742* (2013.01); *A61F 2002/302* (2013.01); *A61F 2002/30138* (2013.01); *A61F 2002/30158* (2013.01); *A61F 2002/30365* (2013.01); *A61F 2002/30369* (2013.01); *A61F 2002/30934* (2013.01); *A61F 2002/443* (2013.01); *A61F 2002/444* (2013.01); *A61F 2002/449* (2013.01); *A61F 2220/0033* (2013.01); *A61F 2230/0017* (2013.01); *A61F 2230/0026* (2013.01); *A61F 2230/0065* (2013.01)

(58) Field of Classification Search
CPC ................................ A61F 2/44; A61F 2/4425
See application file for complete search history.

(56) References Cited

U.S. PATENT DOCUMENTS

| | | |
|---|---|---|
| 3,819,814 A | 6/1974 | Pope |
| 3,864,409 A | 2/1975 | Pope |
| 4,055,862 A | 11/1977 | Farling |
| 4,104,344 A | 8/1978 | Pope et al. |
| 4,163,769 A | 8/1979 | Pope et al. |
| 4,164,794 A | 8/1979 | Spector et al. |
| 4,166,292 A | 9/1979 | Bokros |

(Continued)

FOREIGN PATENT DOCUMENTS

| | | |
|---|---|---|
| JP | 01-308557 | 12/1989 |
| JP | 10-501705 | 2/1998 |

(Continued)

*Primary Examiner* — Andrew Yang
(74) *Attorney, Agent, or Firm* — Pate Peterson PLLC; Brett Peterson

(57) ABSTRACT

An artificial disc is provided which more closely matches the movement of the natural spine. The artificial disc uses one or more projections and corresponding recesses to provide a sliding articulation. The artificial joint is inherently stable in that compressive forces placed on the disc such as the weight placed upon the joint or the tension of surrounding tissues urges the joint towards a neutral position and not farther away from a neutral position.

12 Claims, 42 Drawing Sheets

(56) References Cited

U.S. PATENT DOCUMENTS

| | | |
|---|---|---|
| 4,196,181 A | 4/1980 | Vereschagin et al. |
| 4,289,123 A | 9/1981 | Dunn |
| 4,759,766 A | 7/1988 | Buettner-Janz et al. |
| 4,759,769 A | 7/1988 | Hedman et al. |
| 5,258,031 A | 11/1993 | Salib et al. |
| 5,401,269 A | 3/1995 | Büttner-Janz et al. |
| 5,425,773 A | 6/1995 | Boyd et al. |
| 5,496,318 A | 3/1996 | Howland et al. |
| 5,534,029 A | 7/1996 | Shima |
| 5,562,738 A | 10/1996 | Boyd et al. |
| 5,645,596 A | 7/1997 | Kim et al. |
| 5,645,601 A | 7/1997 | Pope et al. |
| 5,676,701 A | 10/1997 | Yuan et al. |
| 5,725,582 A | 3/1998 | Bevan et al. |
| 5,782,832 A | 7/1998 | Larsen et al. |
| 5,888,226 A | 3/1999 | Rogozinski |
| 5,895,428 A | 4/1999 | Berry |
| 5,899,941 A | 5/1999 | Nishijima et al. |
| 6,010,533 A | 1/2000 | Pope et al. |
| 6,019,792 A | 2/2000 | Cauthen |
| 6,039,763 A | 3/2000 | Shelokov |
| 6,113,637 A | 9/2000 | Gill et al. |
| 6,146,421 A * | 11/2000 | Gordon ............... A61F 2/4425 623/17.15 |
| 6,179,874 B1 | 1/2001 | Cauthen |
| 6,290,726 B1 | 9/2001 | Pope et al. |
| 6,368,350 B1 | 4/2002 | Erickson et al. |
| 6,398,815 B1 | 6/2002 | Pope et al. |
| 6,402,787 B1 | 6/2002 | Pope et al. |
| 6,410,877 B1 | 6/2002 | Dixon et al. |
| 6,425,922 B1 | 7/2002 | Pope et al. |
| 6,488,715 B1 | 12/2002 | Pope et al. |
| 6,494,918 B1 | 12/2002 | Pope et al. |
| 6,497,727 B1 | 12/2002 | Pope et al. |
| 6,514,289 B1 | 2/2003 | Pope et al. |
| 6,517,580 B1 | 2/2003 | Ramadan et al. |
| 6,517,583 B1 | 2/2003 | Pope et al. |
| 6,596,225 B1 | 7/2003 | Pope et al. |
| 6,610,095 B1 | 8/2003 | Pope et al. |
| 6,655,845 B1 | 12/2003 | Pope et al. |
| 6,676,704 B1 | 1/2004 | Pope et al. |
| 6,682,562 B2 | 1/2004 | Viart et al. |
| 6,706,068 B2 | 3/2004 | Ferree |
| 6,709,463 B1 | 3/2004 | Pope et al. |
| 6,740,118 B2 | 5/2004 | Eisermann et al. |
| 6,749,635 B1 | 6/2004 | Bryan |
| 6,770,095 B2 | 8/2004 | Grinberg et al. |
| 6,793,681 B1 | 9/2004 | Pope et al. |
| 6,800,095 B1 | 10/2004 | Pope et al. |
| 6,817,550 B2 | 11/2004 | Taylor et al. |
| 6,846,328 B2 | 1/2005 | Cauthen |
| 6,986,789 B2 | 1/2006 | Schultz et al. |
| 6,997,955 B2 | 2/2006 | Zubok et al. |
| 7,001,433 B2 | 2/2006 | Songer et al. |
| 7,066,958 B2 | 6/2006 | Ferree |
| 7,066,960 B1 | 6/2006 | Dickman |
| 7,077,867 B1 | 7/2006 | Pope et al. |
| 7,083,651 B2 | 8/2006 | Diaz et al. |
| 7,105,024 B2 | 9/2006 | Richelsoph |
| 7,147,665 B1 | 12/2006 | Bryan et al. |
| 7,172,142 B2 | 2/2007 | Taylor et al. |
| 7,270,679 B2 | 9/2007 | Istephanous et al. |
| 7,338,527 B2 | 3/2008 | Blatt et al. |
| 7,396,501 B2 | 7/2008 | Pope et al. |
| 7,396,505 B2 | 7/2008 | Pope et al. |
| 7,461,978 B2 | 12/2008 | Pope et al. |
| 7,465,219 B2 | 12/2008 | Dixon et al. |
| 7,494,507 B2 | 2/2009 | Dixon et al. |
| 7,537,615 B2 | 5/2009 | Lemaire |
| 7,556,763 B2 | 7/2009 | Pope et al. |
| 7,569,176 B2 | 8/2009 | Pope et al. |
| 7,665,898 B2 | 2/2010 | Pope et al. |
| 7,678,325 B2 | 3/2010 | Gardinier |
| 8,016,889 B2 | 9/2011 | Dixon et al. |
| 8,163,023 B2 | 4/2012 | Nguyen et al. |
| 8,449,991 B2 | 5/2013 | Gardinier et al. |
| 8,603,169 B2 | 12/2013 | Nguyen et al. |
| 8,603,181 B2 | 12/2013 | Pope et al. |
| 8,663,359 B2 | 3/2014 | Harding et al. |
| 9,078,763 B2 | 7/2015 | Nguyen et al. |
| 2003/0019106 A1 | 1/2003 | Pope et al. |
| 2003/0078660 A1 | 4/2003 | Clifford et al. |
| 2003/0191533 A1 | 10/2003 | Dixon et al. |
| 2004/0002761 A1 | 1/2004 | Rogers et al. |
| 2004/0111159 A1 | 6/2004 | Pope et al. |
| 2004/0199260 A1 | 10/2004 | Pope et al. |
| 2004/0223676 A1 | 11/2004 | Pope et al. |
| 2004/0243241 A1 | 12/2004 | Istephanous |
| 2005/0033438 A1 | 2/2005 | Schultz et al. |
| 2005/0043802 A1 | 2/2005 | Eisermann et al. |
| 2005/0055098 A1 | 3/2005 | Zdeblick et al. |
| 2005/0087915 A1 | 4/2005 | Pope et al. |
| 2005/0110187 A1 | 5/2005 | Pope et al. |
| 2005/0121417 A1 | 6/2005 | Dixon et al. |
| 2005/0133277 A1 | 6/2005 | Dixon et al. |
| 2005/0146086 A1 | 7/2005 | Pope et al. |
| 2005/0149196 A1 | 7/2005 | Zucherman et al. |
| 2005/0158200 A1 | 7/2005 | Pope et al. |
| 2005/0165487 A1 | 7/2005 | Muhanna et al. |
| 2005/0171610 A1 | 8/2005 | Humphreys et al. |
| 2005/0187633 A1 | 8/2005 | Ferree |
| 2005/0197705 A1 | 9/2005 | Arnin et al. |
| 2005/0203626 A1 | 9/2005 | Sears et al. |
| 2005/0203630 A1 | 9/2005 | Pope et al. |
| 2005/0228497 A1 | 10/2005 | Ferree et al. |
| 2005/0256577 A1 | 11/2005 | Baumgartner et al. |
| 2005/0256578 A1 | 11/2005 | Blatt et al. |
| 2005/0267582 A1 | 12/2005 | Ferree et al. |
| 2006/0004453 A1 | 1/2006 | Bartish, Jr. et al. |
| 2006/0020342 A1 | 1/2006 | Ferree et al. |
| 2006/0041313 A1 | 2/2006 | Allard et al. |
| 2006/0069439 A1 | 3/2006 | Zucherman et al. |
| 2006/0069440 A1 | 3/2006 | Zucherman et al. |
| 2006/0069441 A1 | 3/2006 | Zucherman et al. |
| 2006/0085077 A1 | 4/2006 | Cook et al. |
| 2006/0149372 A1 | 7/2006 | Paxson et al. |
| 2006/0178745 A1 | 8/2006 | Bartish, Jr. et al. |
| 2006/0235530 A1 | 10/2006 | Shelokov |
| 2006/0259147 A1 | 11/2006 | Krishna et al. |
| 2006/0263233 A1 | 11/2006 | Gardinier et al. |
| 2006/0282020 A1 | 12/2006 | Bertagnoli et al. |
| 2007/0010887 A1 | 1/2007 | Williams et al. |
| 2007/0016302 A1 | 1/2007 | Dickman |
| 2007/0021836 A1 | 1/2007 | Doty et al. |
| 2008/0119932 A1 | 5/2008 | Lechmann et al. |
| 2008/0154380 A1 | 6/2008 | Dixon et al. |
| 2008/0195220 A1 | 8/2008 | Pope et al. |
| 2008/0215158 A1 | 9/2008 | Pope et al. |

FOREIGN PATENT DOCUMENTS

| | | |
|---|---|---|
| JP | 11-137585 | 5/1999 |
| JP | 2002-508679 | 3/2002 |
| JP | 2004-329937 | 11/2004 |
| JP | 2005-523109 | 8/2005 |
| JP | 2006-510452 | 3/2006 |
| WO | WO 94/04100 | 3/1994 |
| WO | WO 2005/025431 | 3/2005 |
| WO | WO 2005/089680 | 9/2005 |

* cited by examiner

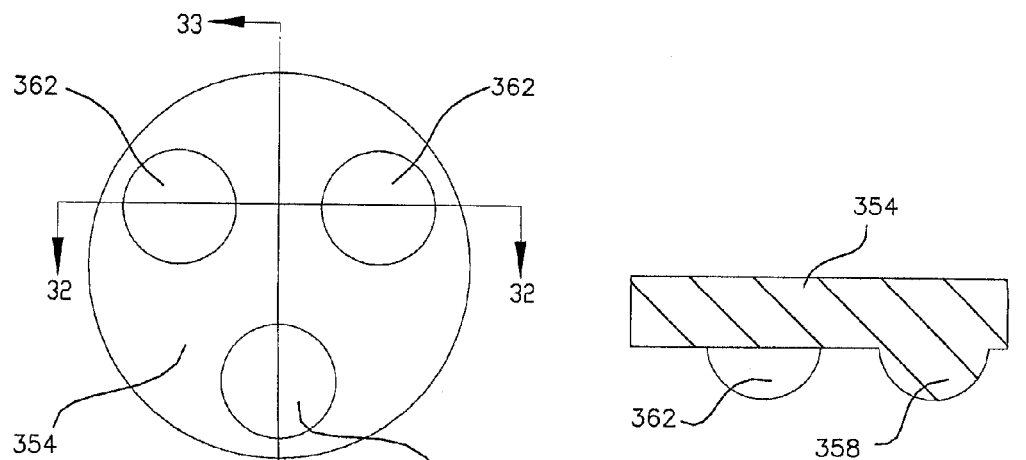
FIG. 31
FIG. 33
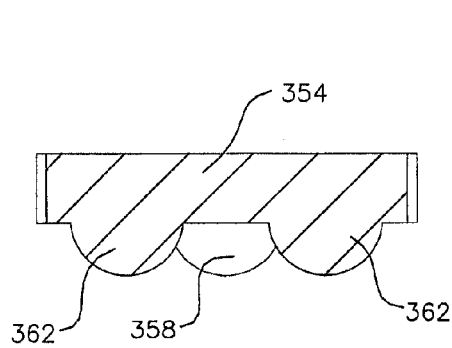
FIG. 32
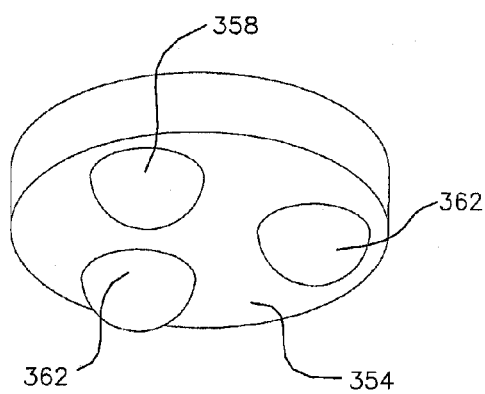
FIG. 34

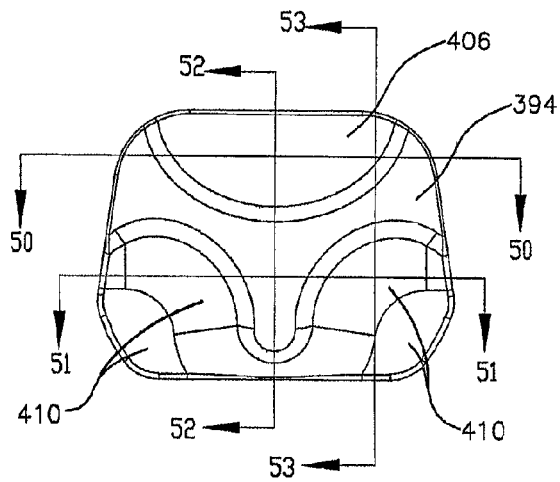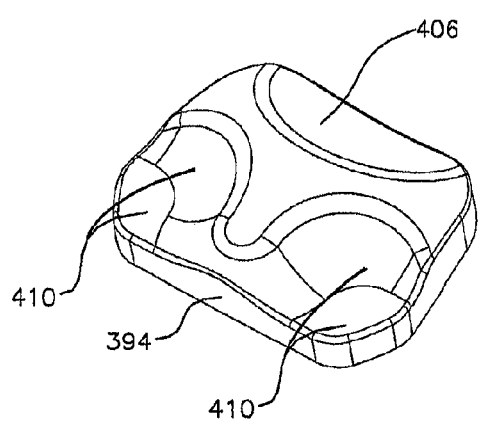
FIG. 49  FIG. 48
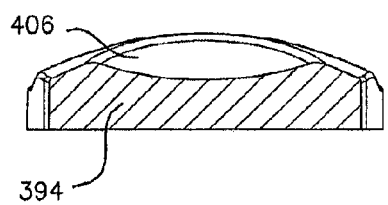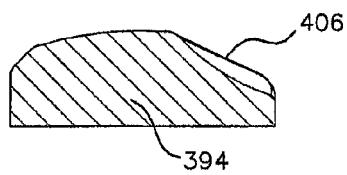
FIG. 50  FIG. 52
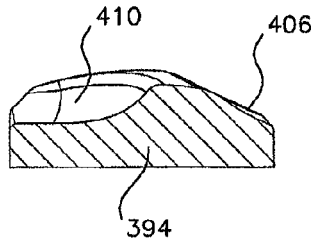
FIG. 51  FIG. 53

MULTI-LOBE ARTIFICIAL SPINE JOINT

RELATED APPLICATIONS

The present application is a continuation application of U.S. patent application Ser. No. 14/099,945, filed Dec. 7, 2013, which is incorporated herein by reference in its entirety, and which is a continuation application of U.S. patent application Ser. No. 13/445,833, filed Apr. 12, 2012, now U.S. Pat. No. 8,603,169, which is incorporated herein by reference in its entirety, and which is a continuation of U.S. patent application Ser. No. 12/028,740, filed Feb. 8, 2008, now U.S. Pat. No. 8,163,023, which is incorporated herein by reference in its entirety, and which claims the benefit of U.S. Provisional Application Ser. No. 60/889,217, filed Feb. 9, 2007, which is incorporated herein by reference in its entirety, and U.S. Provisional Patent Application Ser. No. 60/914,469, filed Apr. 27, 2007, which is incorporated herein by reference in its entirety.

BACKGROUND OF THE INVENTION

1. The Field of the Invention

The present invention relates to artificial joints, and in particular to an artificial inter-vertebral disc for replacement of damaged spinal discs. The present invention relates to an improved artificial inter-vertebral disc for both total disc replacement and for nuclear replacement.

2. State of the Art

Artificial joints are increasingly becoming more common for the medical treatment of degenerated boney joints. Joints may become damaged due to accidents, diseases, aging, etc., and are often replaced when the pain is sufficient, or when natural motion of the joint is sufficiently impaired. Artificial joints commonly replace the tissue between adjoining bones, and may often replace the ends of the two adjoining bones which form the joint.

In replacing a joint, there are generally several desirable outcomes to be achieved. These outcomes include: stability, load bearing capability, natural motion preservation, pain relief, and reduced failure rates and reduction in catastrophic failure. Due to the complexity of the human spine, stability has been a very difficult parameter to address. Often this instability manifests itself as additional wear and premature failure of the artificial joint or supporting physiological structures, adjacent segment/joint degeneration, and exacerbating the pain and disability of the patient.

A number of artificial discs which are presently available tend to lack the stability of the natural spine. Many total disc replacement devices (TDR) are of the "ball in cup" or "ball in trough" design. One of the problems of these particular designs is that the TDR requires the surrounding tissues and structures (ligaments and joints) to provide support and stability. Due to the physical geometry of these designs, the further the spine is moved from the "neutral position" the more the artificial joint has a tendency to continue moving in that direction, thus applying unnatural stress on the surrounding tissues and structures and requiring greater forces to return the joint to the "neutral position." Over time, the constantly applied and increased loads required to operate the artificial joint may lead to damage to the muscles, connected tissues and adjacent structures of the spine, exacerbating the pain and hampering proper movement of the spine. It has also been discovered that, due to the instability of the replaced disc, the spine can develop scoliosis, or curvature, which tends to lead to additional deterioration of the tissues associated with the spine, such as failure of adjacent joints.

The neutral position for a joint is the normal resting position for the joint, and is typically in the middle of the range of motion for a spinal joint. For a typical spine, two adjacent vertebral bodies have endplates which are approximately parallel in the neutral position.

Another parameter that must also be controlled is the ability to mimic the natural kinematic motion of the spine. Many joints in the human body can be adequately approximated by simple joints such as a hinge or a ball in socket. Because of the complex construct of the spinal joint, it cannot be approximated by simple joints. Many prior artificial discs allow the vertebrae to move in a pivotal motion having symmetrical movements. The differences in movement between a natural joint and an artificial joint can cause undesirable effects on the surrounding muscle and tissue. This can cause a degeneration and inability to properly move and control the artificial joint accentuating the instability of the artificial joint, and may accelerate further joint problems.

There is a need for an artificial joint that is more energetically stable with the inherent tendency to return the joint to a "neutral position" in order to reduce the stress and fatigue on the surrounding tissues and structures. Additionally, there is additional need for the artificial joint to more accurately match the natural kinematic motion of the spine to reduce stress and fatigue again on the surrounding tissues and structures. These are but two parameters important to designing a successful spinal disc replacement.

SUMMARY OF THE INVENTION

The objective of the present invention is to provide an improved artificial disc. One objective of the invention is to create an artificial disc that more closely matches the movement of the natural spine. To closely match the natural motion of the spine, one method would be to use non-congruent articulating surfaces that allow for asymmetrical and/or coupled movement. Such an artificial disc would promote long term success of the replaced joint as it maintains more natural motions of the muscles and tissues surrounding the joint. By more closely matching the natural movement, the artificial disc helps prevent degeneration of surrounding tissues and adjacent segment, while promoting better patient mobility of the joint.

A further objective of the present invention is to provide an artificial disc which is more energetically stable. When displaced from a neutral position, the compressive forces naturally applied to the spine such as from gravity and the tension in surrounding tissues urges the artificial joint back into a neutral position and not away from a neutral position. Such an artificial joint is especially beneficial where multiple discs are replaced as it avoids tissue fatigue and joint instability.

These and other aspects of the present invention may be realized in an artificial disc which uses a plurality of projections to engage a mating surface to allow naturally constrained translational and rotational movement between two adjacent vertebrae. The mating surface typically includes a plurality of recesses which receive the projections. The projections are able to slide within the recesses to provide both translational and rotational movement, i.e. flexion/extension, lateral bending, and axial rotation. The projections and recesses are preferably configured to provide coupled translational and rotational movement, causing tilting of a joint member as it slides across the mating joint member. One or more of the projections may also be able to rise partially out of the recess, typically by engaging a wall or sloping portion of the recess, thereby providing an energetically stable system.

Alternatively, other structures such as a single projection and recess having multiple engagement surfaces as described herein may provide the desired relative movement between the top and bottom of the artificial joint. Likewise, intermediate structures between the top and bottom of the artificial joint may be used to provide the desired motion and stability.

BRIEF DESCRIPTION OF THE DRAWINGS

Various embodiments of the present invention are shown and described in reference to the numbered drawings wherein:

FIG. 31 shows a bottom view of the upper portion of the joint of FIG. 30;

FIGS. 32 and 33 show cross sectional views of the upper portion of the joint of FIG. 30 taken along section lines 32 and 33 of FIG. 31;

FIG. 34 shows a bottom perspective view of the upper portion of the joint of FIG. 30;

FIG. 48 shows a perspective view of the lower portion of the joint of FIG. 41;

FIG. 49 shows a top view of the lower portion of the joint of FIG. 41;

FIG. 50 through 53 show cross sectional views of the lower portion of the joint of FIG. 41 taken along section lines 50 through 53 of FIG. 49;

It will be appreciated that the drawings are illustrative and not limiting of the scope of the invention which is defined by the appended claims. The embodiments shown accomplish various aspects and objects of the invention, and any single figure need not accomplish each aspect or advantage of the invention. It is appreciated that it is not possible to clearly show each element and aspect of the invention in a single figure, and as such, multiple figures are presented to separately illustrate the various details of the invention in greater clarity.

DETAILED DESCRIPTION

The invention will now be discussed in reference to the drawings and the numerals provided therein so as to enable one skilled in the art to practice the present invention. The drawings and descriptions are exemplary of various aspects of the invention and are not intended to narrow the scope of the appended claims. In some figures, space is shown between adjacent structures which are normally in contact with each other in order to more clearly show the structures.

Figure 1:
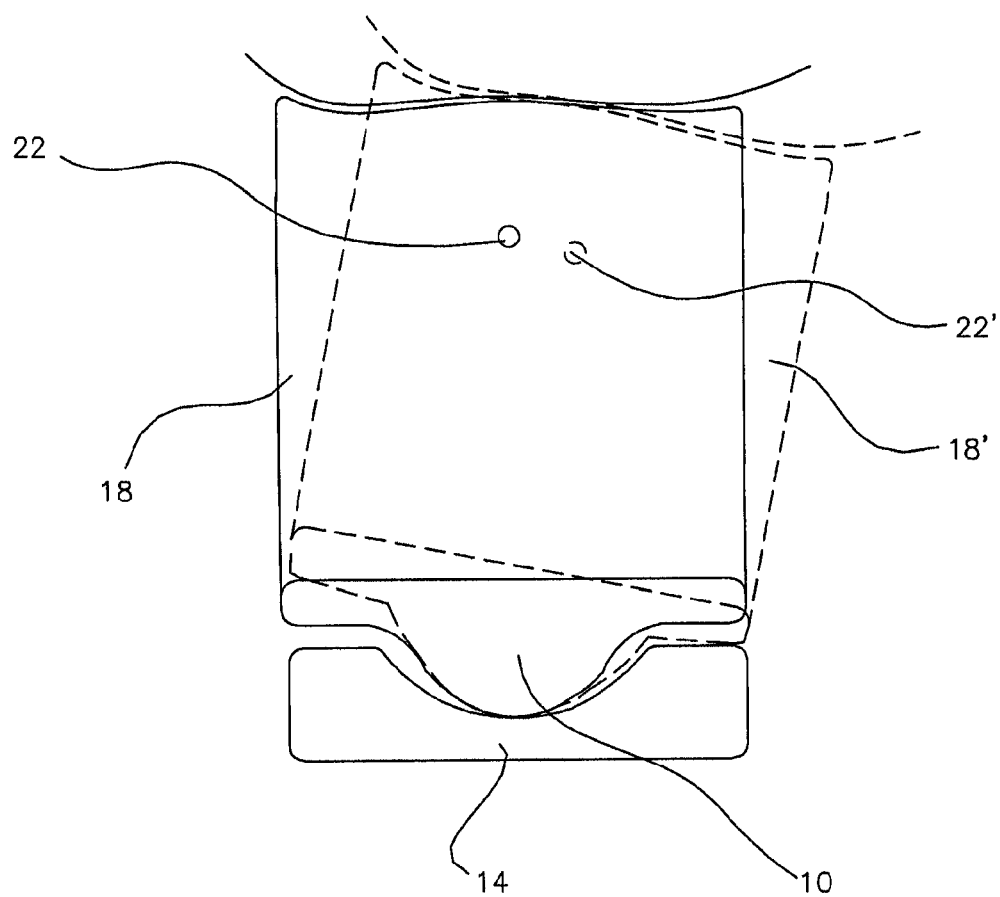
FIG. 1 shows a side view of an art artificial joint in accordance with principles of the prior art.

Currently, a number of artificial discs are presently available or being tested. These tend to lack the stability of the natural spine. These prior art joints typically include a bearing surface which includes a cup shaped receptacle on top of a spherical surface or a ball or spherical surface 10 placed in a cup shaped receptacle 14, as shown in FIG. 1. These joints move by pivoting in a manner similar to other known ball and socket joints. Rectangle 18 generally indicates body mass above the joint (as is supported by the particular joint), such as additional vertebrae, bones, and tissue. Circle 22 indicates a piece of the body weight above the joint, providing a reference point for illustrative purposes. As the ball 10 pivots into position 10', as would occur with the bending of the joint (where the person having the artificial joint is bending), body mass 18 and reference point 22 move to the locations indicated by 18' and 22'. It is appreciated that the position 22' is at a lower vertical height that position 22.

It is thus appreciated that as the joint pivots by rotating ball 10, there is a general lowering of point 22 as it is moved to position 22'. The pivoting of the joint is favored by gravity, as the body mass 18, 22 above the joint is moved into a lower position. Gravity alone will apply a force to continue the movement, moving the body mass 18, 22 into an even lower position. Additional force is required to move the body mass 18, 22 back into its original position. The spine is in a state of compression due to the force of gravity acting on body mass above each joint and due to the tension of the muscles and other tissues surrounding each joint. These compressive forces tend to move the prior art artificial joints away from a neutral position, as the end points of motion represent minimum energy states, i.e. positions where the gravitational potential energy and tensile forces are minimized.

Thus, it is appreciated that the joint shown is a joint which is inherently unstable. Once moved off of a neutral position, compression on the joint as caused by the tension in surrounding tissue or the weight of the body above the joint tends to continue the movement. The prior art joint is stable at the end points of motion rather than in the middle position, meaning that compressive forces on the joint tend to move the joint to the end points of motion rather than to a center position.

The muscular structure and other tissue structures surrounding the prior art joint must hold the joint in a neutral position (i.e. a resting position where the joint is not displaced, where surrounding muscles and tissue are at resting length) against the compressive forces acting upon the spine, such as the force of gravity. As the spinal joints are seldom in a precisely neutral position, the surrounding muscles and tissues may undergo a considerable amount of stress in attempting to hold such an artificial joint in a desired position, such as when the person is sitting or standing vertically. Additionally, the surrounding muscles and tissues must work harder to return the joint to the neutral position after the bending of the spine. This, in turn, can lead to damage to the muscles, connected tissues and adjacent joints/structures of the spine, exacerbating the pain and hampering proper movement of the spine.

It can thus be understood how it is desirable to have an artificial disc which is energetically stable. It is desirable to have an artificial joint where the compressive forces acting on the spine such as the force of gravity acting on the body mass and weight above the joint tend to move the joint back to a neutral position and not away from a neutral position.

Figure 2:
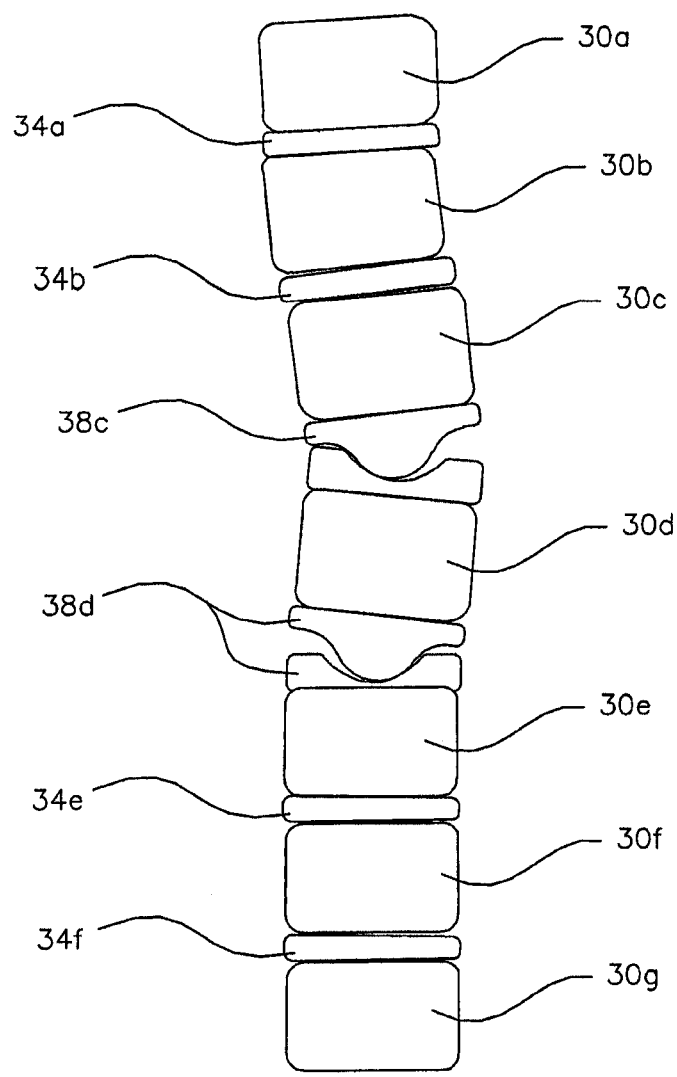
FIG. 2 shows a side view of a spine having multiple prior art artificial joints.

FIG. 2 shows an example of a person's spine which has two or more of the artificial discs of FIG. 1. A plurality of vertebrae 30a-30g and healthy vertebral discs 34a, 34b, 34e, 34f are shown. The natural vertebral discs between vertebrae 30c and 30d, and between vertebrae 30d and 30e have been replaced by prior art artificial discs 38c and 38d, including ball and trough discs as discussed with respect to FIG. 1. As has been discussed, ball and trough discs present inherent instability, where compressive forces such as gravity accentuate movement and pull the joint farther from a neutral position instead of returning the joint to a neutral position.

The problem is increasingly severe with two or more artificial discs as is shown with 38c and 38d. When one artificial disc, such as 38d, is moved from a neutral position, the forces of gravity, unbalanced tension of the body tissues surrounding the spine, etc. cause the second artificial disc 38c to pivot in the opposite direction of 38d. A patient having multiple prior art artificial discs may not be able to maintain their spine in a proper alignment or posture as the artificial discs tend to urge the spine into a bent or collapsed position. Thus, the spine either develops a scoliosis, or curvature, due to the instability of the artificial discs 38c, 38d, and the inability of the body to hold the spine in a proper position, or significantly more stress is placed on the muscles and connective tissue in order for the body to hold the spine in its proper orientation. Over time, the bending or collapsing of the spine due to the artificial discs tends to deteriorate the tissues associated with the spine. It is thus appreciated that where an artificial disc lacks a natural stability, the long term success of the artificial joint is reduced, and is dramatically reduced with increasing numbers of discs being replaced. In fact, the artificial joint may accelerate the failure of otherwise healthy spinal components.

A spine having a single prior art artificial disc may result in a undesired and excessive bending of one or more adjacent natural discs, resulting in a spinal shape similar to that shown in FIG. 2. The undesired bending of the natural discs adjacent to the artificial joint may cause or accelerate degradation of the natural joints, and may result in the need to replace additional discs.

A further concern of an artificial disc is the preservation and restoration of a natural motion. Providing natural motion with an artificial joint is important for multiple reasons, such as providing comfortable movement to the person. Perhaps more important is the effect the artificial joint can have on the surrounding tissue. If the motion is unnatural, the tissues responsible for moving the joint, such as the surrounding muscles, tendons, etc. may be adversely affected by the joint. The surrounding tissue may be unable to properly control the joint, or may gradually degenerate due to the changed movement of the artificial joint. Thus, providing an artificial joint with a natural motion can have a significant effect on the long term success of an artificial joint.

Many artificial joints, such as artificial knees or hips, are relatively simple joints with relatively simple motion, such as hinge or ball in socket type joints. Vertebrae and the natural discs, however, have a complex motion. The natural discs are a soft pad, not unlike a mattress. The natural discs allow for and support the movement of the vertebrae, and allow the vertebrae to shift across the disc with combinations of horizontal, vertical and rotational movement to accomplish the normal movements of the spine.

Prior art artificial discs such as that shown in FIGS. 1 and 2 do not match the natural movement of the spine well. Many prior art artificial discs allow the vertebrae to move in a pivotal motion, and have symmetrical forwards and backwards movement. As has been mentioned, the differences in movement between a natural joint and an artificial joint can cause undesirable effects on the surrounding muscle and tissue. The muscle and tissue are oriented and accustomed to move the joint in a natural motion, and may degenerate or be unable to properly control the artificial joint having an unnatural motion. This degeneration and inability to properly move and control the artificial joint accentuates the instability of the prior art artificial joint, and may cause or accentuate the joint problems discussed with respect to FIGS. 1 and 2.

It can thus be appreciated how it is desirable to have an artificial disc which results in a joint which is energetically stable and which provides a natural motion. Achieving such results provides an artificial disc and resulting joint which minimizes adverse effects on the body such as degradation of the surrounding tissues responsible for controlling the joint and the failure of the joint to provide support to the body in a natural position.

A study of the movement of the cervical spine (the neck) reveals that the kinematic motion of the spine is a complex and asymmetrical movement. The movement of the spine is observed to be a coupling of translational and rotational motion of the vertebral bodies. Herein, the motion of the spine is typically described by describing the motion of the portion of the vertebral body above the relevant spinal disc relative to the corresponding portion of the vertebral body below the disc. Flexion/extension involves the translation of the vertebral body forwards or backwards in combination with rotation of the vertebral body in the same direction of translation. Rotation typically involves rotation of the vertebral body about a point somewhat behind the center of the vertebral body in combination with some lifting and some sideways tilting, the vertebral body tilting to the left somewhat during a left rotation, etc. Lateral bending (side to side) is accomplished by cooperation of multiple vertebral joints in a combination of rotation, flexion/extension, and lateral tilting. The motion of the natural spine has been described by: Panjabi et al, Spine. 2001 Dec. 15; 26(24):2692-700; Ishii et al., Spine. 2006 Jan. 15; 31(2):155-60; Ishii et al, Spine. 2004 Dec. 15; 29(24):2826-31; and Ishii et al, Spine. 2004 Apr. 1; 29(7):E139-44.

Figure 3:
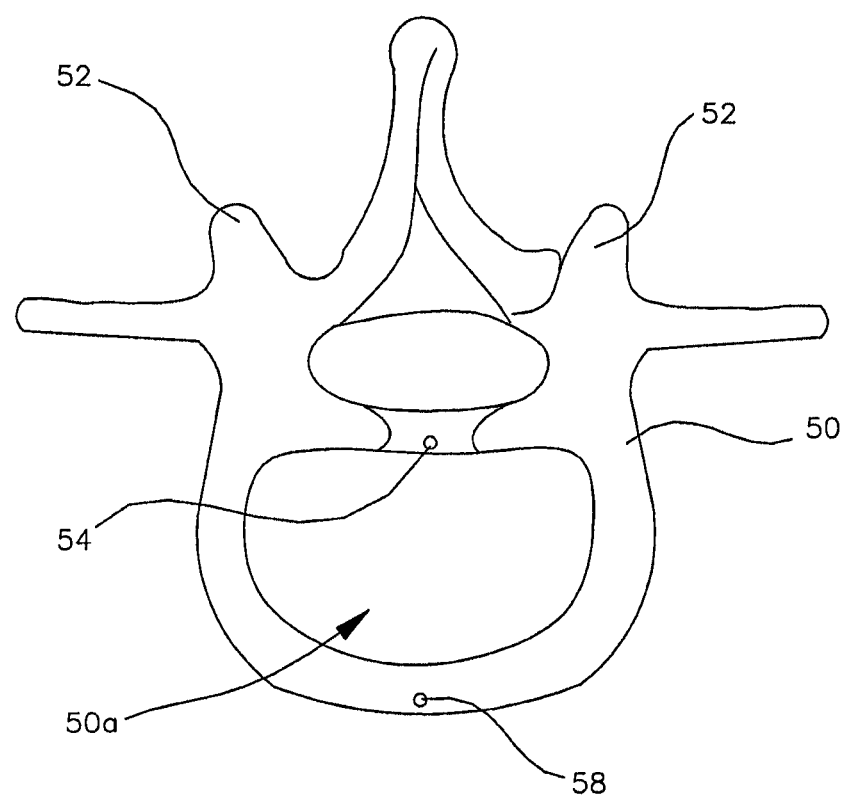
FIG. 3 shows a top view of a vertebra of a human.

FIG. 3 shows a top view of a vertebra 50. The vertebra includes various structures for the attachment of surrounding tissue, the passage of the spinal column, etc. As the present invention concerns the vertebral discs and providing an artificial disc, the drawings and discussion of the vertebra will typically be limited to the vertebral body, the rounded frontal area indicated at 50a which connects to the vertebral disc. Thus, the present application shows the vertebral bodies as rounded or cylindrical sections for simplicity. The posterior (back) of the disc area of the vertebra is indicated at point 54, and the anterior (front) is indicated at 58. The facet joints 52 aid in controlling the motion of the natural spine as is generally understood. These points are referred to in discussing the movement of the vertebra.

Figure 4:
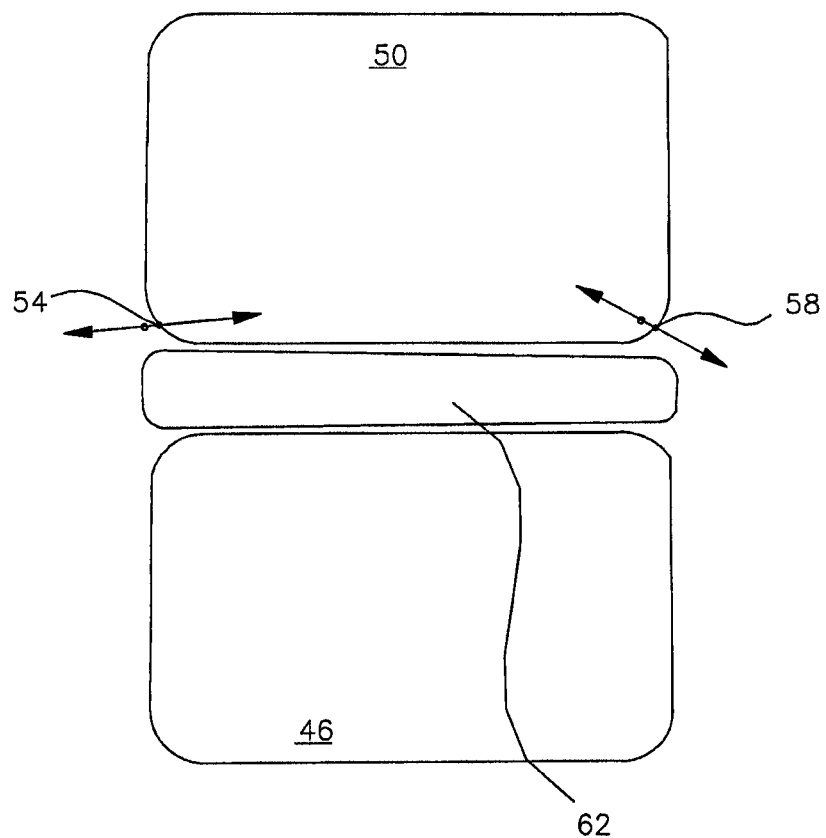
FIG. 4 shows a schematic side view of two vertebrae illustrating the vertebral motion in forwards and backwards flexion/extension of the spine.

FIG. 4 shows a side (lateral) view of two vertebrae, showing typical movements of a cervical vertebra in flexing/extending forwards and backwards. It is observed that the posterior 54 and anterior 58 of the vertebra 50 move differently relative to vertebra 46. The anterior 58 of vertebra 50 exhibits a greater amount of vertical movement than the posterior 54 of vertebra 50. It is also observed that the movement of vertebra 50 involves a considerable amount of sliding movement relative to vertebra 46. The disc 62 between the vertebrae is quite conforming, and changes shape to allow for the movement of the vertebrae, such as for the forward and backward movement of the vertebra 50. While the present invention discusses the artificial joint in the context of a joint for cervical disc replacement, it will be appreciated that it may be used for replacing other spinal discs as well, typically by modifying the size of the artificial joint and possibly by modification of the shape of the projections and recesses slightly to control the motion and achieve a desired range of motion.

Figure 5A:
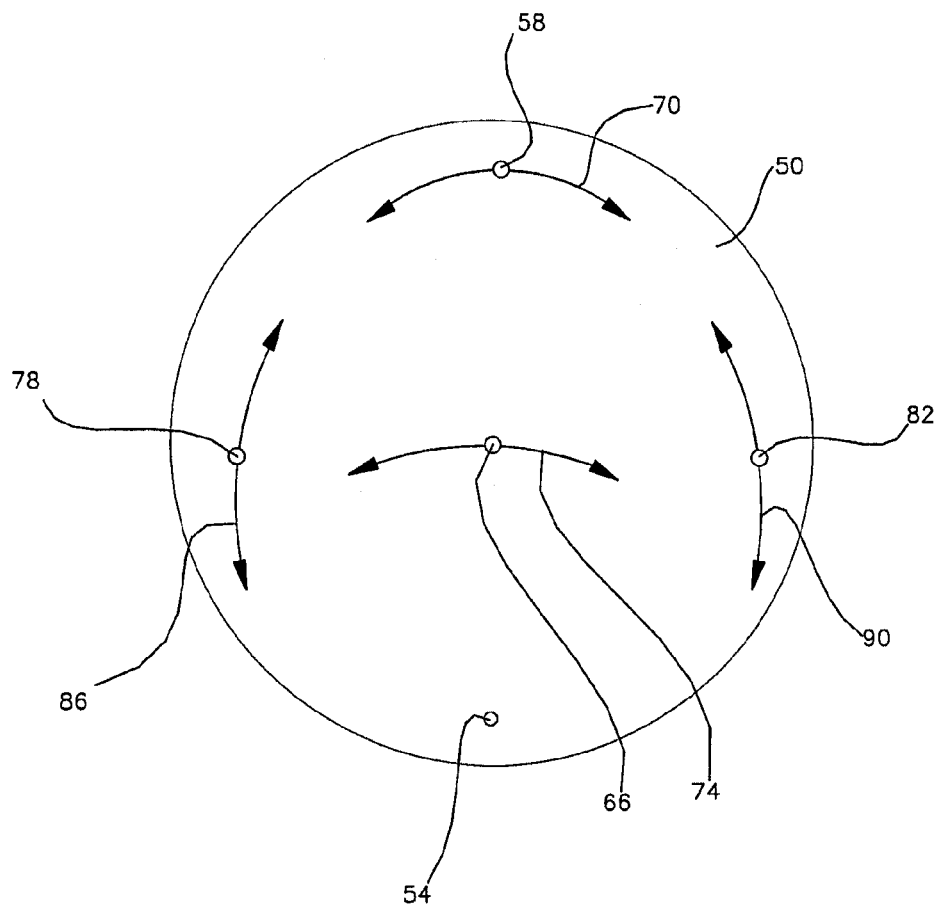
FIG. 5A shows a schematic top view of a vertebra illustrating the vertebral motion in lateral bending of the spine.

FIG. 5A shows a top view of vertebra 50, illustrating the horizontal movement of various points of the vertebra during lateral bending. The posterior 54 of the vertebra 50 remains in substantially the same location during lateral bending. The anterior 58 and center 66 of the vertebra 50 pivot relative to the posterior 54 of the vertebra, moving in arcuate movements as indicated by arrows 70 and 74. The left side 78 and right side 82 of the vertebra 50 also move in arcuate movements as though pivoting around the posterior 54 of the vertebra, indicated by arrows 86 and 90.

Figure 5B:
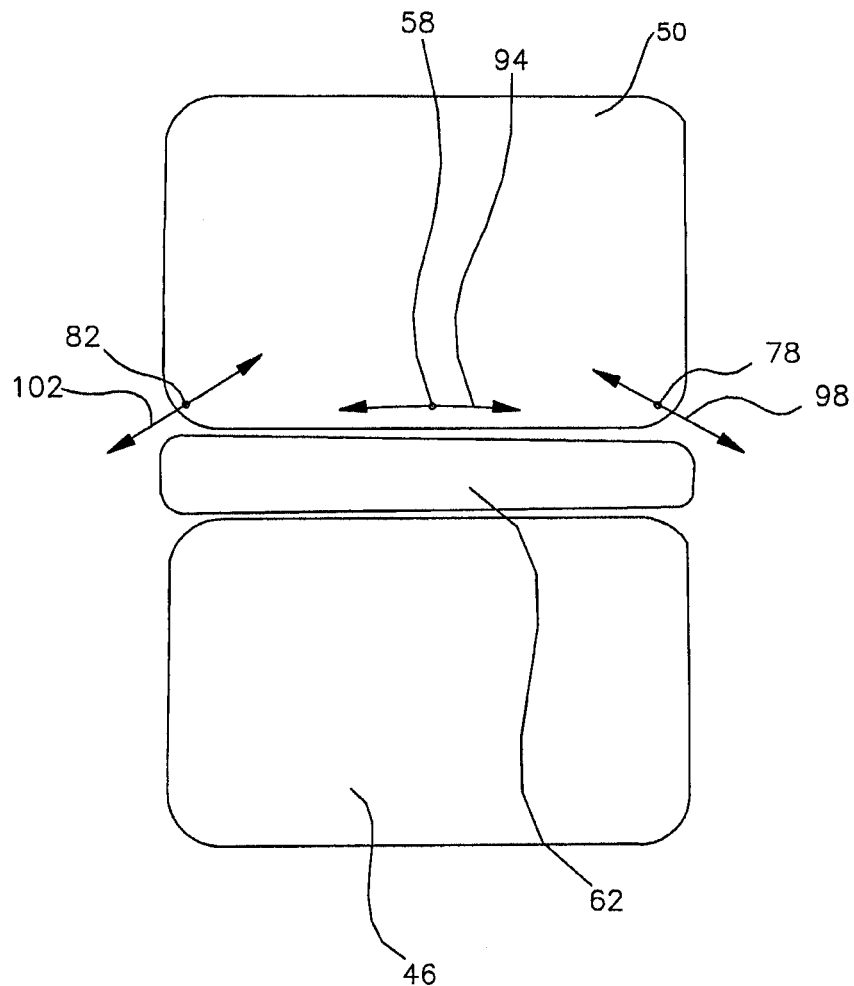
FIG. 5B shows a schematic side view of two vertebrae illustrating the vertebral motion in lateral bending of the spine.

FIG. 5B shows a front view of the vertebra 50, illustrating the vertical movement of various points of the vertebra during lateral bending. Vertebra 46 and disc 62 are also shown so as to illustrate the movement of vertebra 50 relative to vertebra 46. In lateral bending, the anterior 58 of vertebra 50 moves horizontally relative to vertebra 46, as indicated by arrow 94. Left side 78 and right side 82 of vertebra 50 move vertically as well as horizontally, as indicated by arrows 98 and 102.

As illustrated by FIGS. 5A and 5B, lateral bending of the vertebra 50 is a complex movement. The vertebra 50 both slides and twists sideways. The vertebra 50 slides across the disc 62, pivoting around a posterior point 54 of the vertebra 50. As the left side 78 or right side 82 of the vertebra 50 move sideways, they move vertically, twisting the vertebra 50 relative to vertebra 46. As mentioned above, lateral bending typically involves coordinated movements of multiple spinal joints to achieve the desired movement. FIGS. 5A and 5B describe a desired movement of a single spine joint in order to accommodate the natural lateral bending of the spine.

Figure 6A:
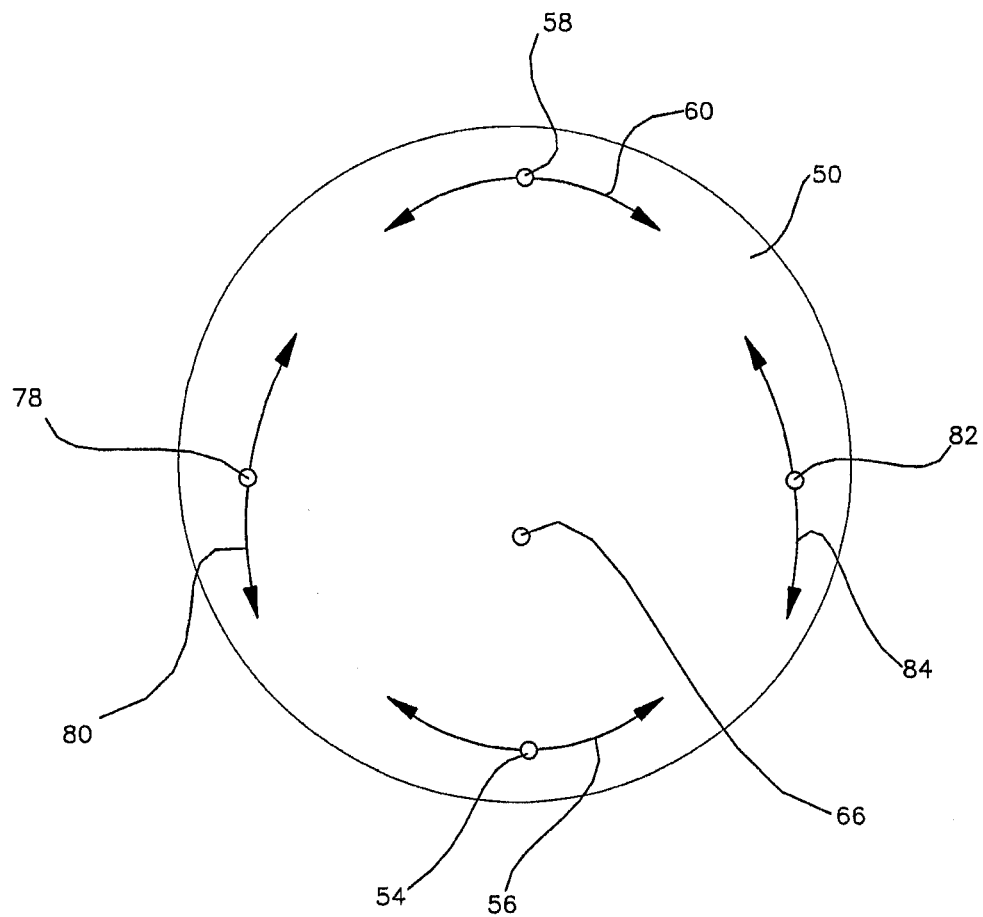
FIG. 6A shows a schematic top view of a vertebra illustrating the vertebral motion during rotation of the spine.
Figure 6B:
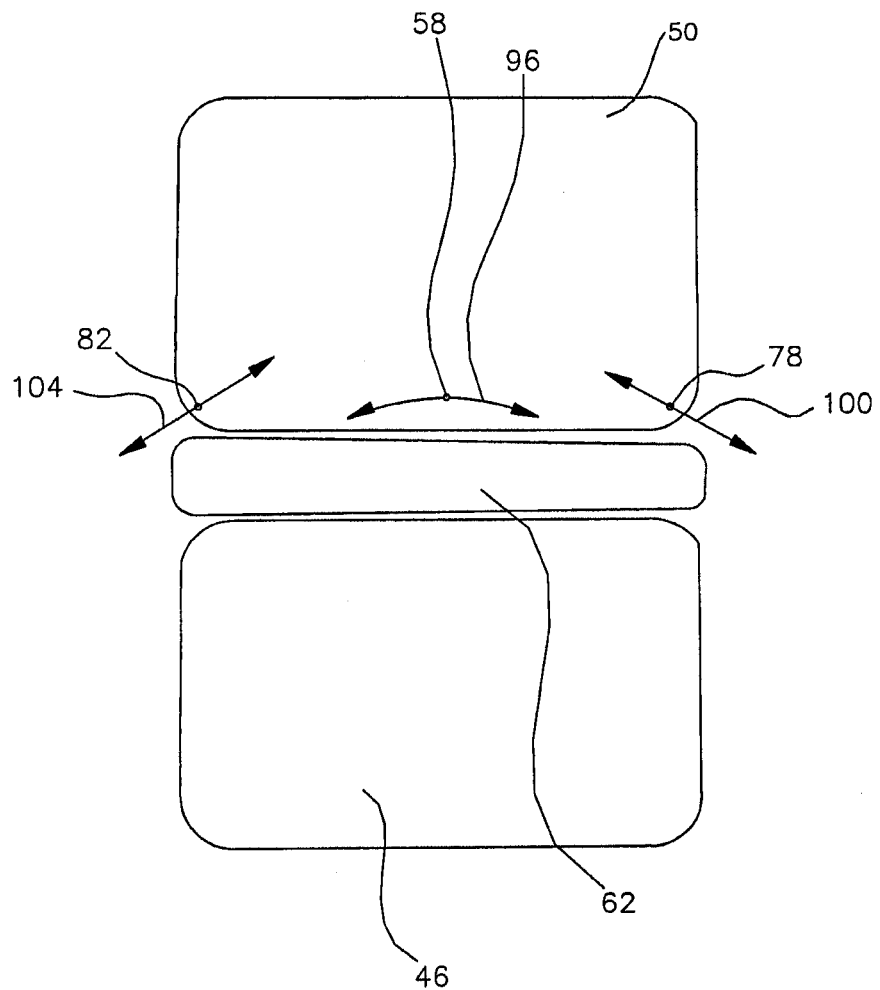
FIG. 6B shows a schematic side view of two vertebra illustrating the vertebral motion in rotation of the spine.

FIG. 6A shows a top view of the vertebra 50 illustrating the horizontal movement of various points of the vertebra during rotation of the vertebra 50. The vertebra 50 rotates about a point 66 slightly behind the center of the vertebra. As such, the anterior point 58, posterior point 54, and lateral points 78, 82 move according to arrows 56, 60, 80, 84 as shown. FIG. 6B shows a front view of the vertebra 50 as well as vertebra 46 and disc 62, illustrating the horizontal movements of the vertebra 50 during rotation thereof. The vertebra 50 undergoes some vertical lifting as wells as tilting towards the side of rotation (i.e. tilting to the left side during a left rotation) as is indicated by arrows 96, 100, 104.

Figure 7A:
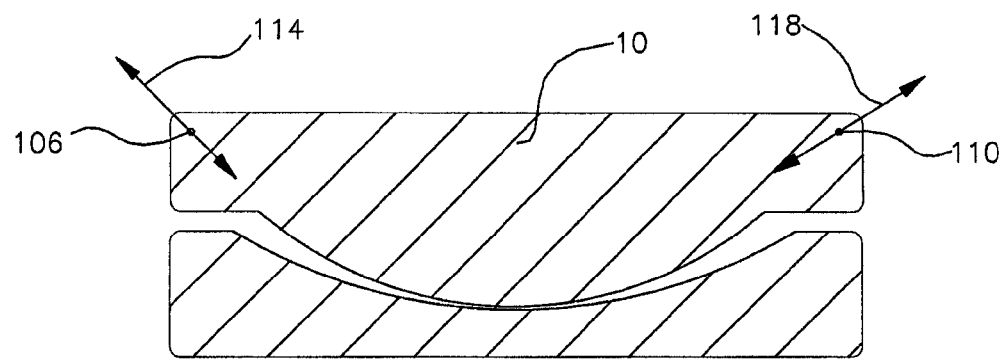
FIGS. 7A and 7B show the motion of the prior art artificial joint of FIG. 1 in flexion and rotation.

Prior art artificial discs, such as that shown in FIG. 1, involve a ball and socket type configuration, or a hemispherical disc between two sockets, etc. It is appreciated that the prior art artificial vertebra of FIG. 1 does not move in a similar fashion as the natural vertebra as discussed in FIGS. 3-6. FIG. 7A shows the movement of the prior art artificial disc which is typical to both flexion/extension and lateral bending. The posterior 106 and anterior 110 of the upper vertebral surface 10 move according to the arrows 114, 118. It is appreciated that this movement is quite different than the flexing/extending movement and lateral bending movement of the natural spine as shown in FIG. 4. The lateral bending movement of the artificial disc is similar to the flexing movement, whereas the natural spine bends laterally with a combination of rotation and flexing movement. The compressive forces present in the body (such as the weight of the body and the tension of the muscles and tendons, etc.) tend to return a natural vertebra to a neutral flexing position, where compressive forces applied to the prior art artificial disc tend to move the prior art disc to an extreme flexing or bending position, away from the neutral position.

Figure 7B:
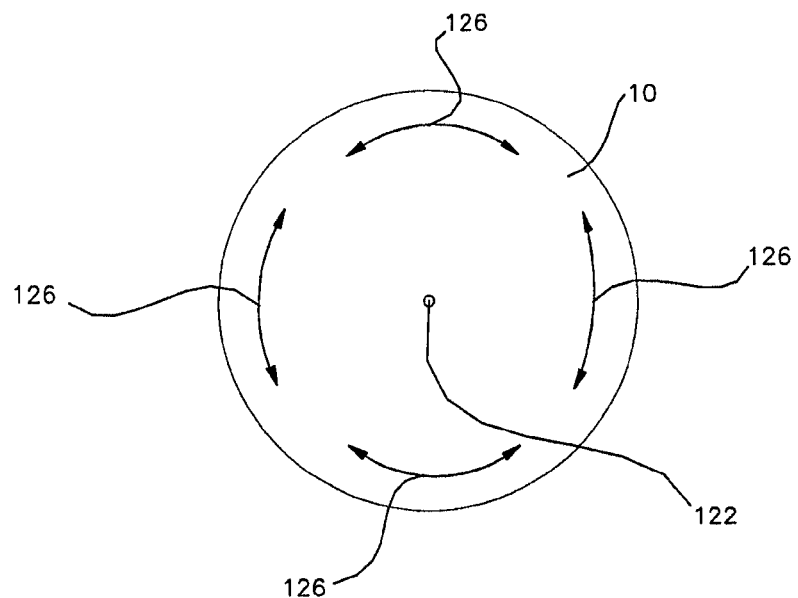

FIG. 7B shows a top view of the prior art artificial disc of FIG. 1 illustrating the rotational movement of the resulting joint. The upper vertebral surface 10 pivots about the center 122 as shown by arrows 126. The ball and socket type artificial disc pivots about the center of the disc and pivots without any vertical movement of the disc. As shown in FIGS. 5 and 6, a natural vertebra pivots about a point more towards the rear of the disc in combination with some lifting and tilting, which the prior art artificial discs do not adequately replicate. The compressive forces present in the body (such as gravity and muscle tension, etc.) bias the natural vertebra into a neutral pivotal position, while the prior art artificial vertebra is not biased into a neutral position.

It is thus better appreciated how the prior art artificial disc results in joints which lack inherent stability (can not center themselves or are not biased to a neutral position by the natural compressive forces acting on the spine) and which fail to recreate the movement of the natural spine. Both of these factors result in unnatural movement and place additional stress on the muscles, connective tissues, and supporting joints which operate the particular spinal joint. Thus, the prior art artificial disc can contribute to further failure of the spine.

Figure 8:
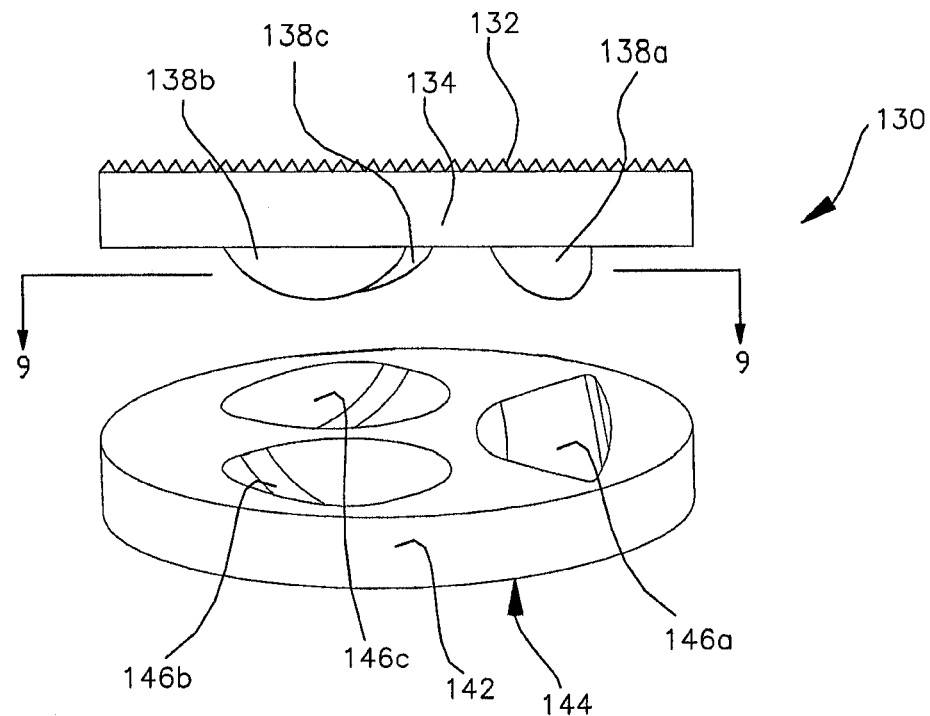
FIG. 8 shows a disassembled perspective view of an artificial disc of the present invention.

Turning now to FIG. 8, a disassembled perspective view of an artificial joint 130 according to the present invention is shown. The joint 130 includes an upper portion 134 having a plurality of projections 138a, 138b, 138c (generally 138) and a lower portion 142 having a plurality of recesses 146a, 146b, 146c (generally 146). The projections 138 are received in the recesses 146 when the artificial joint is assembled to replace a disc in the spine. The recesses 146 define the surface which the projections 138 contact and define the possible ranges of movement of the projections, and thus the movement of the upper surface 134 relative to the lower surface 142. The interaction between the surface of the projections and the surface of the recesses provides controlled movement of the artificial joint 130 which more closely resembles the movement of the natural spine.

In showing the present invention in the following figures and in discussing the present invention, the recesses and projections are often denoted by a bounded area. It is appreciated from the following discussion and figures that the projections and recesses are often smoothly contoured and transition gradually from the surrounding material. Thus, there may not be a sharply defined edge to the projection or recess. The defined boundaries of the recess, for example, may represent the area in which the projection is intended to move, or the area which contacts the projection during expected use of the artificial joint. In some configurations of the artificial joint, the projection or recess may have a more sharply defined edge, such as when a retaining wall is used to provide a positive limit to the range of motion of the artificial joint. In other configurations, the recess may be unbounded or have no distinct edge, and may have another structure such as a pin to limit the movement of the upper surface relative to the lower surface. Thus, it is understood that the term recess is used broadly to define the general area or portion which receives a projection, and is not intended to limit the structure to a structure having opposing sidewalls or an elongate nature.

The following figures and description will better describe the profiles of the projections 138 and recesses 146 and the resulting range and types of movement allowed by the artificial disc 130. It will be appreciated by the figures and discussion that the recesses 146 need not necessarily have steeply sloped vertical edges to as to absolutely contain the projection 138, but may present a gradual transition from the adjacent surface of the lower surface 142. The term recess is used to describe the surfaces which are contacted by the projections 138 and across which the projections slide to allow for movement of the artificial disc 130.

The upper surface 132 of the upper portion 134 and the lower surface 144 (not visible) of the lower portion 142 are configured for attachment to bone to thereby form an artificial joint. Thus, the attachment surfaces 132, 144 may have spikes, porous structure, chemicals to induce bonding to the bone, etc. as is known in the prior art. These surfaces are not detailed in every drawing, but are understood to be part of all of the artificial joints disclosed herein as may be necessary. Additionally, the base of the upper portion 134 and/or lower portion 142 may be tapered in thickness such that the resulting artificial disc 130 is wedge shaped and not flat. A wedge shaped artificial disc is useful in addressing lordosis, kyphosis, scoliosis, or other conditions present in a patient's spine. The use of artificial joint elements having a tapered thickness so as to produce a wedge shaped artificial disc is understood to be part of all of the artificial joints disclosed herein. It will be appreciated that such attachment structures or tapering thicknesses may not be necessary in all situations, or may often be of a different size or configuration, especially in situations such as where the artificial joint is sized for a nuclear replacement.

Figure 9:
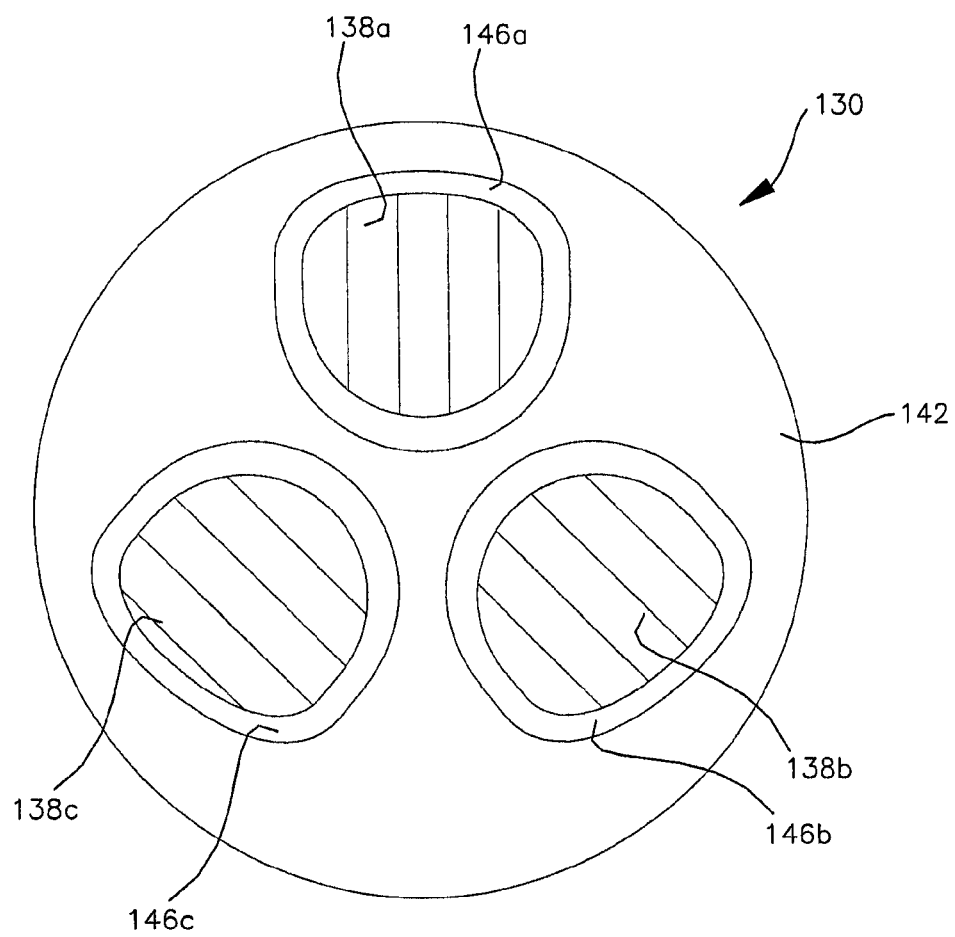
FIG. 9 shows a partially cut-away top view of an artificial disc of the present invention taken along line 9-9 of FIG. 8.

FIG. 9 shows a partially cut-away top view of the joint 130, illustrating one possible configuration of the projections 138 and recesses 146. The lower portion 142 and recesses 146, as well as a cross-sectional view of the projections 138 are visible. The remainder of the upper portion 134 is omitted for clarity. (While discussed in this application as the projections extending downwardly from the upper portion into the recesses in the lower portion, it will be appreciated that the configuration can be reversed so that the projections extend upwardly from the lower portion into receptacles in the upper portion while maintaining the stability discussed herein).

FIG. 9, and many of the following figures are taken along line 9-9 of FIG. 8, and are used to indicate the shapes and orientation of the projections and recesses and configuration of the artificial joint.

The projections 138 are formed as hemispherical projections on the upper portion 134, and are illustrated with cross-hatching to distinguish from the recesses 146. The recesses 146 are formed in the lower portion 142. The recesses may be formed as hemispherical recesses, or may be formed as oval, kidney, or egg shaped recesses. For example, the anterior recess 146a may be formed as an oval recess having a long axis extending sideways. The lateral recesses 146b, 146c may be formed as oval recesses having a long axis extending somewhat parallel to the adjacent edge of the lower layer 142. Regardless of the shape, it is preferred that the recesses be larger from side to side than adjacent portions of the associated projection so that the projection is provided some degree of translational movement prior to engaging the sidewalls (which are generally sloped rather than vertical) of the recesses.

As is more specifically illustrated in subsequent figures, the receptacles are typically contoured to control the movement of the resulting artificial joint. Typically, the bottom portion of the receptacles 146 is relatively flat to allow some translational movement, and the inward sides of the receptacles are increasingly sloped to cause a lifting of the upper portion 134 as a particular side thereof slides towards the center of the lower portion 142. The outer portions of the receptacles 146 may simply continue in the direction of the lower portion of the receptacles, or may contain a retaining wall or steeply sloped surface which limits the motion of the artificial joint 130. It is not intended that the projections 138 will climb such a sloped outer portion of the receptacles 146 so as to lift the side of the upper portion 134 which is moving away from the center of the lower portion 142 as such is typically contrary to the motion of the natural spine.

Additionally, the recesses 146 may be oriented at various angles to aid in controlling the movement of the joint. The anterior recess 146a may be oriented so as to be directed somewhat forwards rather than completely vertically. The lateral recesses 146b, 146c, may be oriented somewhat backwards and out the lateral sides.

Figure 10:
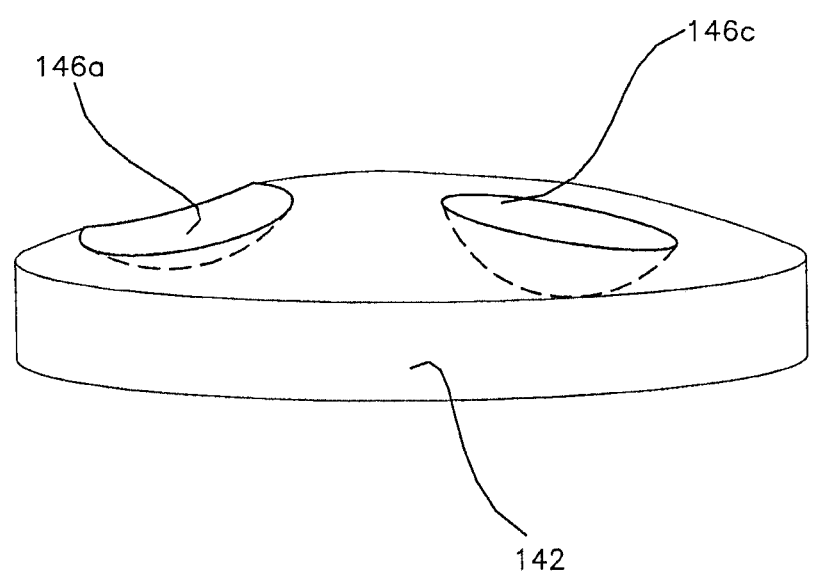
FIG. 10 shows a side view of the base portion of the artificial disc of FIG. 9.

FIG. 10 shows a side view of the lower portion 142 of FIG. 9. It can be more clearly seen how the anterior recess 146a is oriented in a forwards direction rather than completely vertically, and how the lateral recesses 146b (not shown), 146c are oriented such that they are tilted outwardly and backwards from a completely vertical orientation. The orientation of the recesses 146 aids in controlling the movement of the projections and upper portion; thus controlling the movement of the artificial disc 130. The movement of the artificial disc 130 will be discussed in greater detail in the following figures and description.

Figure 11:
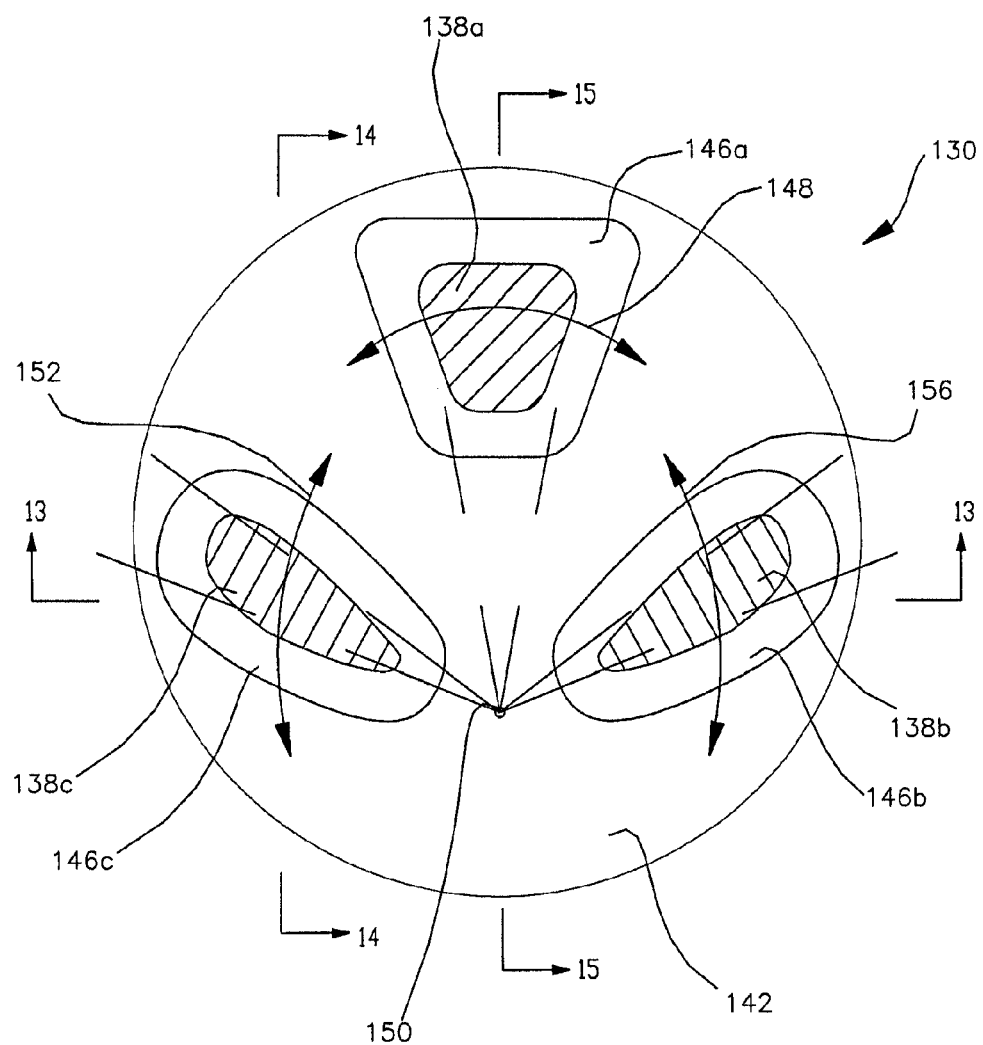
FIG. 11 shows a top view of a base portion and a cross-sectional view of the projections of an artificial disc of the present invention.

FIG. 11 shows another partially cut-away top view of the artificial disc 130, illustrating an alternate configuration of the projections 138 and recesses 146. The projections 138 are formed so as to have sides which are generally aligned in a radial alignment with a posterior point 150, as indicated by the dashed reference lines extending from the posterior point 150. Similarly, the contours of the receptacles 146 generally follow those radial lines. Such a radial alignment encourages the disc to rotate about the posterior point 150, imitating the movement of the natural spine as discussed above.

As the disc rotates, the anterior projection 138a moves laterally as is illustrated by arrow 148, and the lateral projections 138b, 138c move as illustrated by arrows 152 and 156. As the upper portion 134 rotates to the right, left lateral projection 138c is raised vertically (out of the page) as it engages the sidewall of the recess, thereby imitating the tilting of the natural spine during rotation. When the upper surface 134 is rotated to the left relative to the lower surface 142 the right lateral projection 138b is raised in a similar manner. These movements are also shown in FIGS. 13-15.

Figure 12:
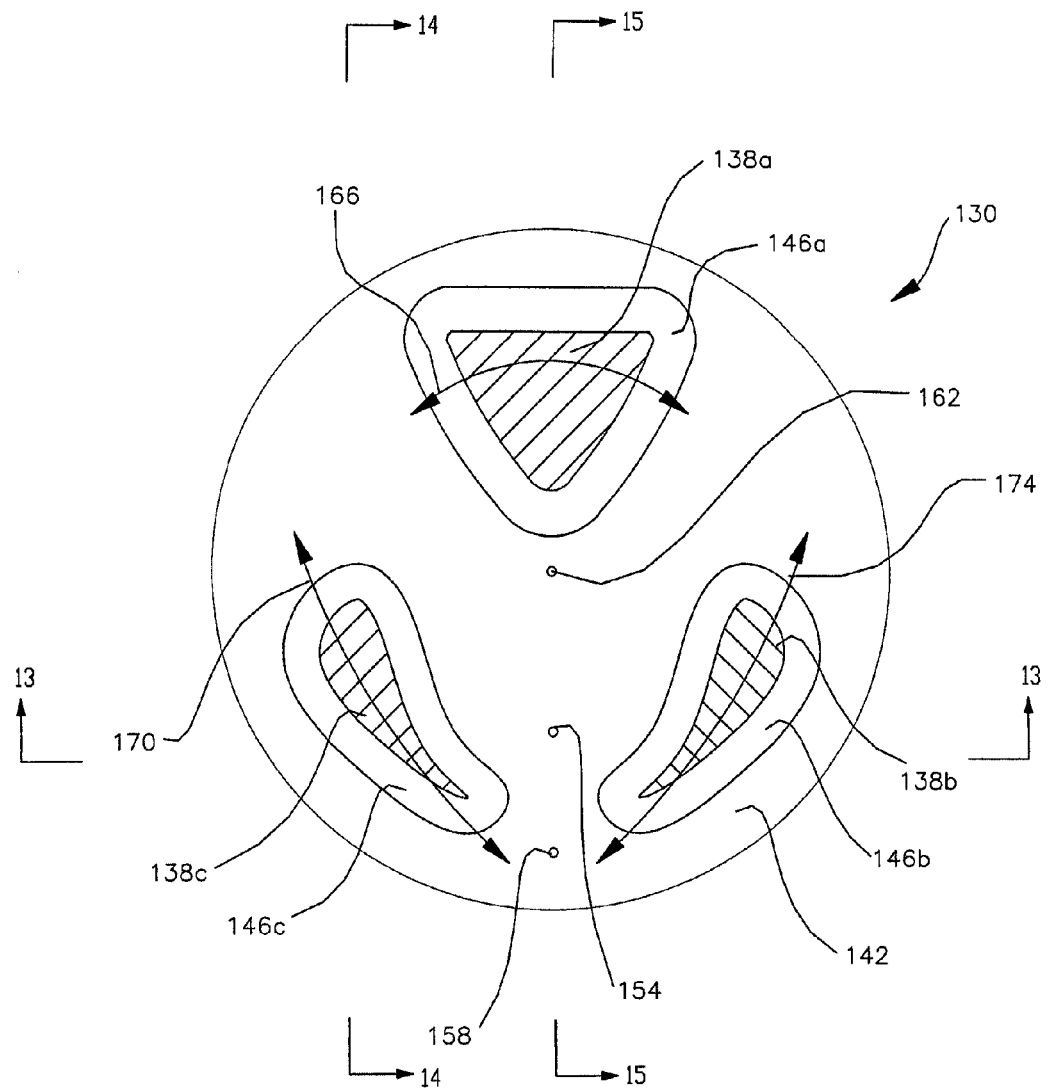
FIG. 12 shows a top view of a base portion and a cross-sectional view of the projections of an artificial disc of the present invention.

FIG. 12 shows another partially cut-away view of the artificial disc 130, illustrating an alternate configuration of the projections 138 and recesses 146. The lateral projections 138b, 138c, and lateral recesses 146b, 146c have been formed such that they are slightly curved. The curve encourages the upper portion 134 to rotate around point 154 relative to the lower portion 142. The curved surfaces of the lateral projections 138b, 138c, and lateral recesses 146b, 146c aid in constraining the rotational movement of the disc 130 to a predetermined motion.

Point 154 is somewhat forward of the posterior portion (indicated at point 158) of the disc 130, but behind the center 162 of the disc. As the upper portion 134 of the disc 130 is rotated, the anterior projection 138a moves according to arrow 166, and the lateral projections move according to arrows 170 and 174. The shape of the recess 146c cause the left lateral projection 138c to be raised vertically when the upper portion 134 is pivoted to the right, and the shape of the recess 146b causes the right lateral projection 138b to rise when the upper portion is pivoted to the left—thus imitating the tilting of the natural spine when rotating.

Figure 13A:
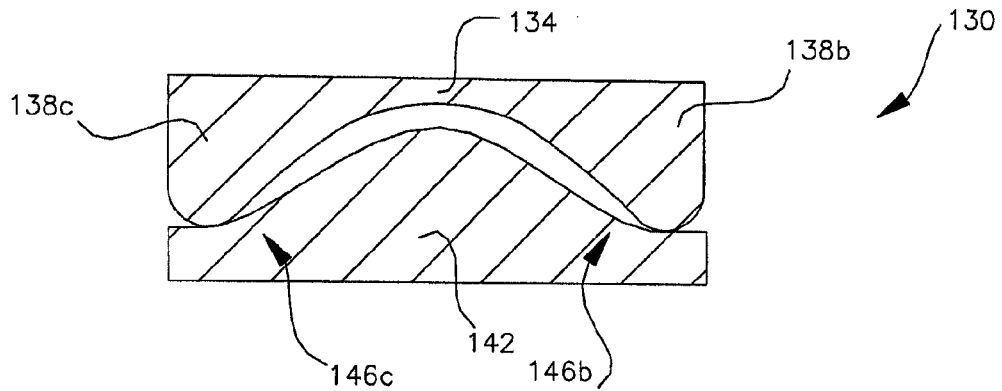
FIG. 13A shows a cross-sectional view of the artificial discs of FIGS. 8 through 12 taken along line 13-13 of FIG. 12.

FIG. 13A shows a cross-sectional view of the artificial discs 130 of FIGS. 8 through 12 along line 13-13 (as indicated in FIG. 12). The cross section shows both the upper portion 134 and lower portion 142 of the artificial disc 130 as included in FIG. 8, but the section line is shown in FIG. 12 for clarity in indicating the section shown. It can be observed how the projections 138b and 138c have rounded lower surfaces to allow for smooth sliding movement (rotation and translation) across the surfaces of the recesses 146b, 146c. The recesses 146b, 146c are also smoothly formed, providing for smooth and continuous movement across a desired range of movement. In a resting position the bottom of the projections 138b, 138c rest on the generally flat bottoms of the recesses 146b, 146c. Thus, the joint is highly stable, as it requires no additional work for the joint to be held in a resting state. The compressive forces exerted on the joint, such as that of the weight of the body and the tension of surrounding tissues, will tend to bias the joint into such a resting state. The joint's resting state is energetically stable (an energetic minimum) and corresponds to the neutral position of the natural spine.

When the upper portion 134 is slid to the right relative to the lower portion 142 (as occurs in the natural spine), the left projection 138c is raised as it travels upwardly along the surface of recess 146c. The right projection 138b moves generally horizontally across the generally flat bottom of recess 146b, resulting in a tilting of the upper portion 134 to match that of the natural spine, and resulting in a net expansion of the artificial disc. Left movement of the upper surface 134 causes the right projection 138b to be raised vertically along the sidewall of the recess 146b, while the left projection 138c slides generally horizontally, tilting the upper portion 134 to the left and resulting in a net expansion of the artificial disc. By matching the travel and curvature of the projections 138 with the sidewalls of the recesses 146, the upper surface 134 can be made to closely resemble the travel which occurs in the natural spine. It is thus appreciated that the compressive forces placed on the spine such as the weight of the body above the artificial joint and the tension in the tissues surrounding the natural spine will urge the artificial joint back into the neutral position, as these forces act to compress the artificial joint. The artificial joint 130 is thus naturally stable as these compressive forces tend to return the upper portion 134 to its original neutral position. Thus, additional fatigue is not placed on the muscles and connective tissue, increasing joint stability.

Figure 13B:
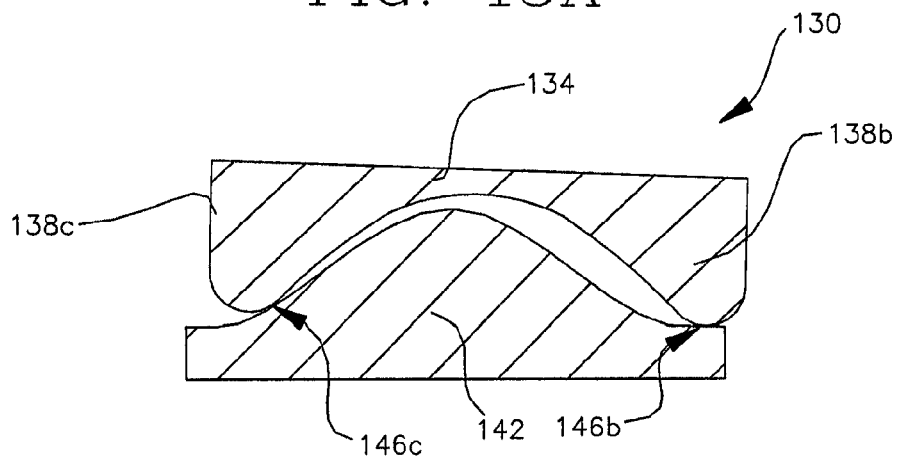
FIG. 13B shows another cross-sectional view of the artificial disc of 13A, with the projections having been moved in the troughs to thereby change the angle of the upper portion of the artificial disc.

FIG. 13B shows the artificial joint of FIG. 13A with the upper portion displaced slightly to the right. It can be seen how the projection 138c is raised as it moves to the right and how the upper portion 134 is tilted to the right. It can be seen how the average distance between the upper portion 134 and lower portion 138 is increased, resulting in a net expansion of the artificial joint. Thus, compressive forces acting on the joint 130 counteract the expansion of the joint and return it to a neutral position.

The expansion of the artificial joint caused by movement thereof may be described in different ways. The volume occupied by the joint, including the volume of the upper portion 134, lower portion 138, and the space directly therebetween, increases in response to displacement of the joint from a neutral position. Alternatively, the mean distance between the upper portion 134 and the lower portion 142 increases when the joint is displaced from a neutral position. While various different terms may be used to describe the expansion of the joint 130, the design of the artificial spinal disc of the present invention is such that, for the intended range of motion of the resulting artificial joint, the artificial joint is expanded as a result of the displacement of the joint from a neutral position and therefore compressive forces placed on the artificial joint will bias the joint back into a neutral position. This produces a joint which is inherently stable as the forces normally placed on the joint while in use tend to restore the joint to a neutral position. For the most preferred embodiments of the artificial joint, the joint experiences a net expansion for all types of desired movement, resulting in a joint where all types of movement are counteracted by compression of the joint, and thus a joint where the compression naturally placed on the spine biases the joint into a neutral position in reaction to all types of movement from neutral.

Figure 13C:
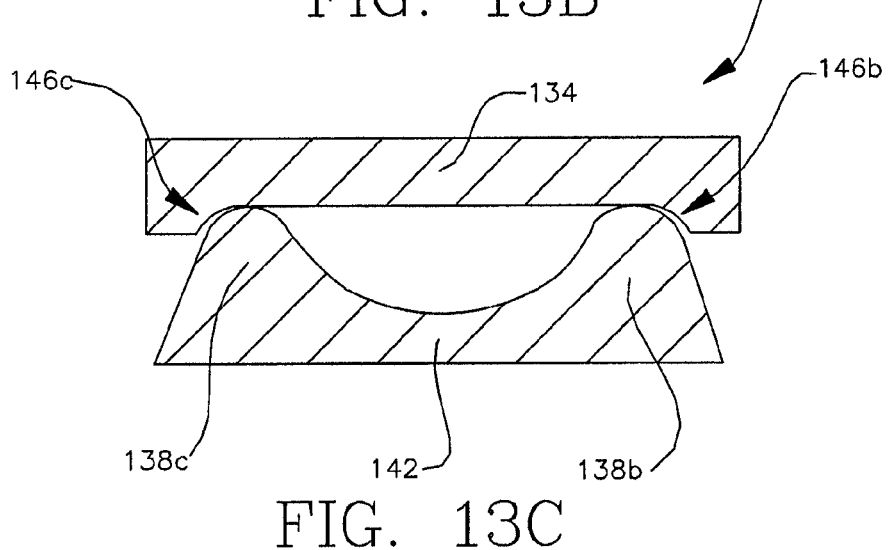
FIG. 13C shows another cross-sectional view of an artificial disc of the present invention.

FIG. 13C shows an artificial joint similar to that of FIGS. 13A and 13B, but where the projections 138 (lateral projections 138b, 138c shown) are formed on the lower portion 142 and the recesses 146 (lateral recesses 146b, 146c shown) are formed on the upper portion 134. It is seen that the direction of slope of the recesses 146 is reversed to achieve the same direction of tilt during movement of the artificial joint 130. That is that where FIG. 13A shows recesses where the sections adjacent the outer edges of the lower portion are generally horizontal and the sections adjacent the interior of the lower portion are sloped, FIG. 13C shows recesses 146 where the sections adjacent the outer edges of the upper portion 134 are sloped and the sections adjacent the interior of the upper portion are generally horizontal. The arrangement shown in FIG. 13C ensures that the upper portion 134 is tilted forwards when extending forwards, etc. to match the natural movement of the spine as has been discussed.

It is thus appreciated that the artificial joints of the present invention may not always have projections 138 on the upper portion 134 and recesses 146 on the lower portion 142, but may contain projections on the lower portion and recesses on the upper portion, or a combination of both projections and recesses on the upper portion and on the upper portion. Generally, when it is desirable to have a projection 138 on the lower portion 142 of the joint and a recess 146 on the upper portion 134 of the joint, the relative orientation of the recess is reversed so that sloping portions which were placed on the inside of the recess (nearest the center of the joint) are placed on the outside of the recess and generally planar or less sloped portions which were placed on the outside portion of the recess are placed on the inside portion of the recess. In most cases, however, it is easier to manufacture an artificial joint where the projections are on the top of the joint and the recesses are on the bottom of the joint.

Figure 14A:
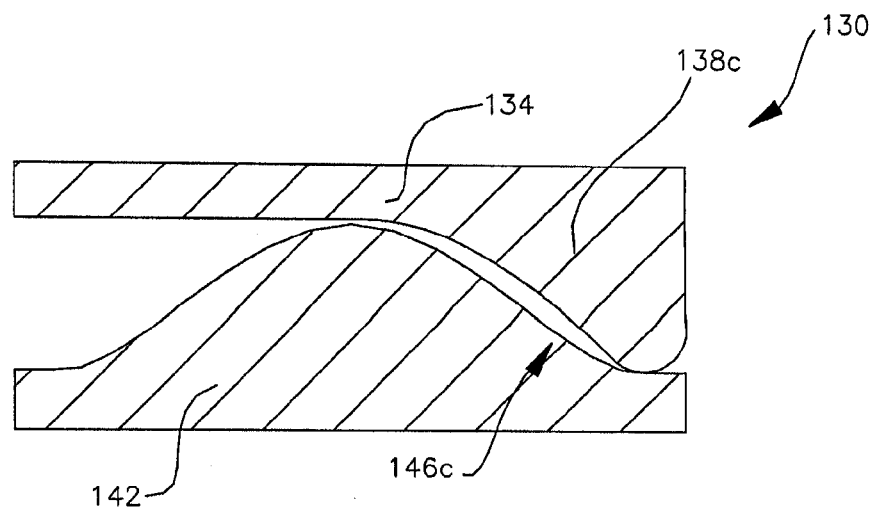
FIG. 14A shows a cross-sectional view of the artificial discs of FIGS. 8 through 12 taken along line 14-14 of FIG. 12.
Figure 14B:
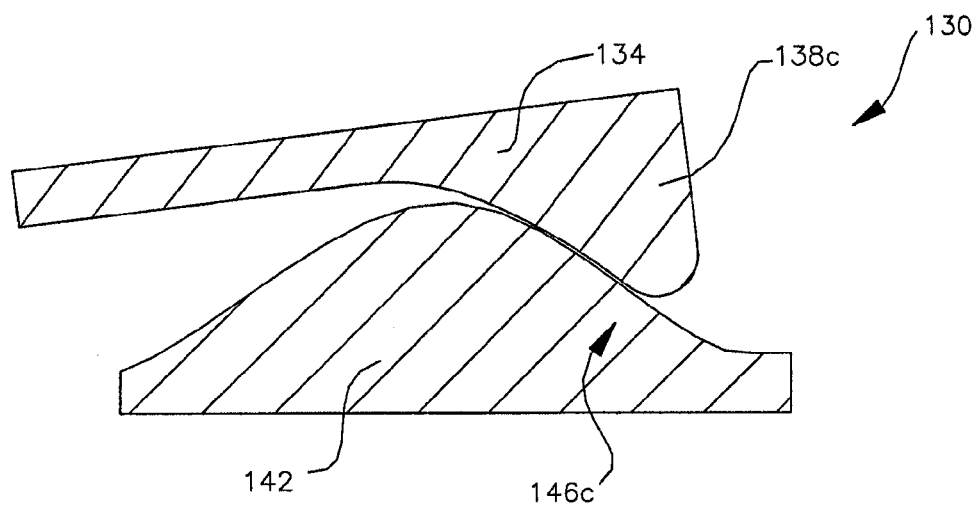
FIG. 14B shows another cross-sectional view of the artificial disc of FIG. 14A, with the projection having been moved in the trough to thereby change the angle of the upper portion of the artificial disc.
Figure 15:
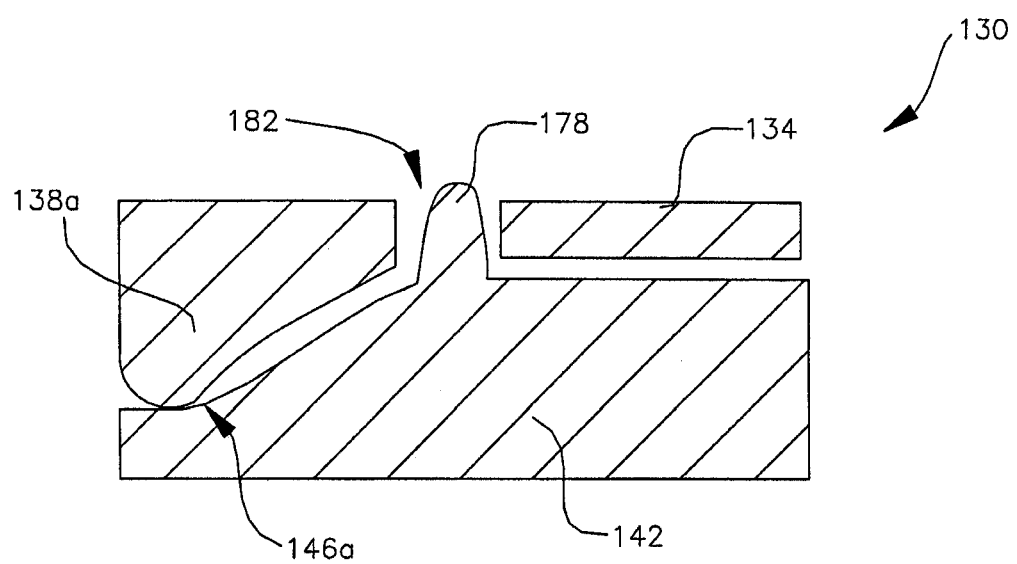
FIG. 15 shows a cross-sectional view of the artificial discs of FIGS. 8 through 12 taken along line 15-15 of FIG. 12.

FIGS. 14A and 14B show cross-sectional views of the artificial discs 130 of FIGS. 8 through 12 along line 14-14. The cross section shows both the upper portion 134 and lower portion 142 of the artificial disc 130 as included in FIGS. 8 through 12, but the section line is shown in FIG. 12 for clarity in indicating the section shown. It can be seen how the lateral projections 138b, 138c (right lateral projection 138b not shown) move upwardly as the upper portion 134 is moved forwards (towards the anterior of the lower surface 142). The lateral projection 138b, 138c slides upwardly and forwards across the surface of the recess 146b, 146c. Thus, the upper portion 134 is pivoted upwardly at the rear about 5-7 degrees, thereby simulating the movement of the natural spine. The anterior projection 138a, not shown, may either slide horizontally, or may even slide downwardly along the slope in the anterior recess 146 to provide the diving motion at the front of the joint similar to a natural spine. Unlike prior art artificial joints, however, the joint is configured to return to its original position once the associated muscles are released, using the compressive forces acting on the joint to slide the projections 138b and 138c back down the sidewalls of their associated recesses, and to slide or raise the anterior projection 138a back to its original position.

FIG. 15 shows a cross-sectional view of the artificial discs 130 of FIGS. 8 through 12 along line 15-15, with the addition of a motion limiting post or stop which is not shown in the previous figures. The cross section shows both the top and bottom of the artificial disc as included in FIGS. 8 through 12, but the section line is shown in FIG. 12 for clarity in indicating the section shown. The anterior projection 138a and recess 146a are visible. As the upper portion 134 moves backwards (towards the posterior of the lower surface) the anterior projection 138a is raised vertically as it slides up the inclined surface of the recess 146a. In order to limit the movement of the upper portion 134 relative to the lower portion 142, one of the upper portion and lower portion may have a post 178 formed thereon (not shown in previous figures) and the other portion may have a corresponding hole 182 or receptacle to receive the post 178.

Various different methods and structures may be used to affirmatively limit the motion of the artificial joint.

The limiting of the movement of the post 178 to space defined by the hole 182 constrains the movement of the upper surface 134 relative to the lower surface 142, and thus constrains the range of motion provided by the artificial disc 130. This may be important in preventing the artificial disc 130 from being dislocated (the upper surface 134 moving too far across or off of the lower surface 142) as may occur in an accident or other forceful impact.

The movement of the cervical vertebrae is relatively small. For example, in flexing/extending forwards and backwards, a vertebra may tilt forwards by about 10 degrees and backwards by about 5 degrees. The same movement may typically involve the vertebra sliding about 1 or 2 millimeters relative to the vertebra below. In rotating, the vertebra may pivot by about 4 degrees and slide about 0.5 or 1 millimeter relative to the vertebra below. Thus, the hole 182 may be about 4 millimeters larger than the diameter than the post 178.

FIGS. 13-15 illustrate how the recesses 146 are shaped to both direct the movement of the projections 138 into predetermined directions and to selectively raise one or more of the projections as the upper portion 134 is moved. The projections are directed into movements which imitate the motion of the natural spine. As the artificial disc 130 is flexed forwards, the upper portion 134 slides forwards and is also tilted forwards as the lateral projections 138b, 138c are raised vertically by recesses 146b, 146c.

As the artificial disc rotates, the projections 138 and recesses 146 also aid in imitating the movement of the natural spine. For example, when the upper portion 134 is rotated to the right, the anterior projection 138a will slide to the right, the left lateral projection 138c will slide to the left and somewhat forwards, and will be raised vertically, and the right projection 138b will slide to the left and slightly backwards. By controlling the shape of the projections 138 and the shape and curvature of the bottom and sidewalls of the recesses 146, the three dimensional movements of the upper portion 134 and the lower portion 142 can be carefully controlled. Thus, an artificial joint can be created which much more closely simulates the movements of the natural spine than the artificial joint of FIG. 1.

Figure 16:
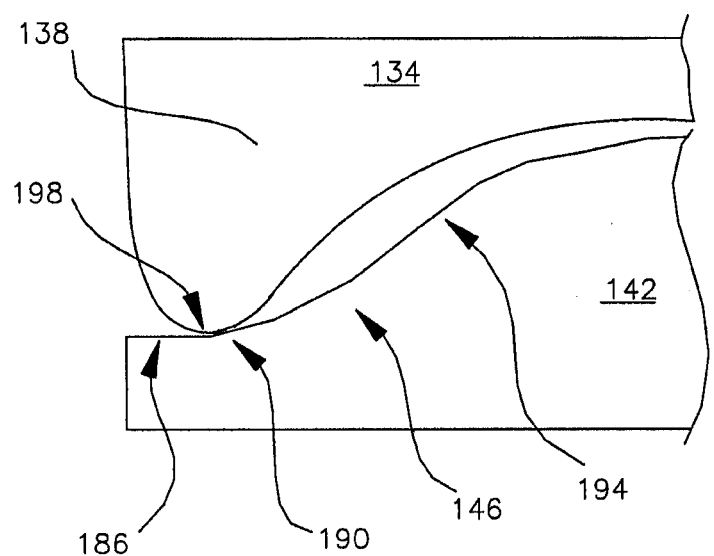
FIG. 16 shows a close-up cross-sectional view of a projection and trough of the artificial disc of the present invention.

FIG. 16 shows a detailed view of a projection 138 and recess 146 of the artificial disc 130. Only one projection 138 and recess 146 are shown for clarity, but the principles discussed apply to each of the projection 138/recess 146 combinations. The recesses 146 may be formed with a generally flat and horizontal lower section 186, a curving transitional section 190, and a more steeply inclined section 194. The projection 138 is formed with a rounded end 198 which may slide smoothly across the recess 146 including transitioning smoothly across the various sections of the recess. It will be appreciated that different shapes of projections and recesses, such as curving sections 190 which curve more rapidly or slowly to increase the rate of rise of the upper portion 134 relative to the translational movement thereof, may be used to alter the characteristic motion of the artificial joint.

The projection 138 may be located in a resting position in the transitional section 190 of the recess, such that the projection 138 will slide in a generally horizontal direction when sliding away from the inclined portion 194 (to the left in FIG. 16), and such that the projection will immediately begin to move upwards as well as horizontally as the projection slides towards the inclined portion of the recess 146 (to the right in FIG. 16). Such a configuration of the projections 138 and recesses 146 may be used to create an artificial disc which is self centering and energetically stable.

The projections 138 and recesses 146 may be oriented such that the projections slide generally horizontally when sliding generally away from the center of the lower portion 142, and such that the projections slide both horizontally and upwardly when sliding generally towards the center of the lower layer 142. Thus, when the artificial disc is moved forwards, as would occur in a forwards flexion of the spine, the anterior projection 138a slides generally forwards and the lateral projections slide both forwards and upwards across the transitional portion 190 and inclined portion 194 of the lateral recesses 138b, 138c. Thus, the posterior portion of the upper layer 134 of the artificial disc 130 is raised upwardly, causing a rising of the body weight and tissue supported above the artificial disc 134. The raising of the upper portion 134 and the weight supported thereon is against the force of gravity and against the tension of the muscles and tissues supporting the spine. Thus, the compressive forces of the body weight placed on the joint and the tension in the supporting tissue will cause the joint to return to a neutral position, lowering the elevated lateral projections 138b, 138c and lowering the upper portion 134 and supported weight. A similar mode of operation is achieved in rotational movement of the artificial disc 130.

While discussed relative to forward flexion, it will be appreciated that each recess 146 may be provided with sloped sidewalls about the entire circumference, thereby selectively controlling the lifting of an associated projection 138 in response to any direction of horizontal movement. By matching the curvature of the projections 138 and the curvature of the recesses 146, substantial control of the three dimension movement of the upper portion 134 is provided.

The artificial disc 130 is thus advantageous over the prior art, as the disc results in a joint which is energetically stable or self centering and which is biased back into a neutral position, where prior art artificial discs result in joints which are gravitationally unstable and biased further from a neutral position once moved from neutral. Additionally, the artificial joints 130 results in a motion which closely approximates the natural motion of the spine. Matching more closely the natural motion of the spine reduces the adverse impact on the tissue surrounding the artificial joint when in use and promotes the long term success of the artificial joint.

Figure 17:
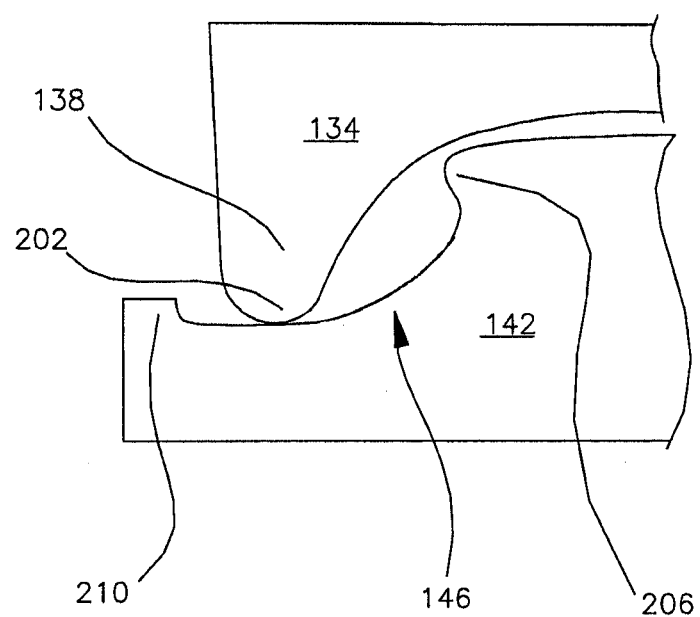
FIG. 17 shows another detailed cross-sectional view of a projection and trough of the artificial disc of the present invention.

FIG. 17 illustrates an alternate configuration of a projection 138 and recess 146 of the artificial disc 130 to limit the range of motion of the resulting joint. The projection 138 has been formed with a rounded end 202 which more steeply curves away from the contact point with the recess 146. The recess 146 has been formed with an inner retaining wall 206 and an outer retaining wall 210. The projection 138 will contact one of the retaining walls after moving to an extreme position within the recess 146. Any or all of the recesses may be thus formed with retaining walls to limit the movement of the upper surface 134 relative to the lower surface 142. Thus, the space between the retaining walls 206, 210 and the projections 138 when the projection is in a resting position will determine range of motion of the upper surface 134, and of the joint resulting from the artificial disc 130.

The retaining walls 206, 210 may extend completely around the recess 146 and connect each other, or may be formed as separate structures. It will be appreciated that inner retaining walls 206 may not be necessary. If each of the recesses 146 is formed with an outer retaining wall 210, the range of movement of the projections 138 and upper surface 134 will be limited in all directions by the outer retaining walls 210. Similarly, outer retaining walls may not be necessary if the joint is completely restrained by inner retaining walls.

Figure 18:
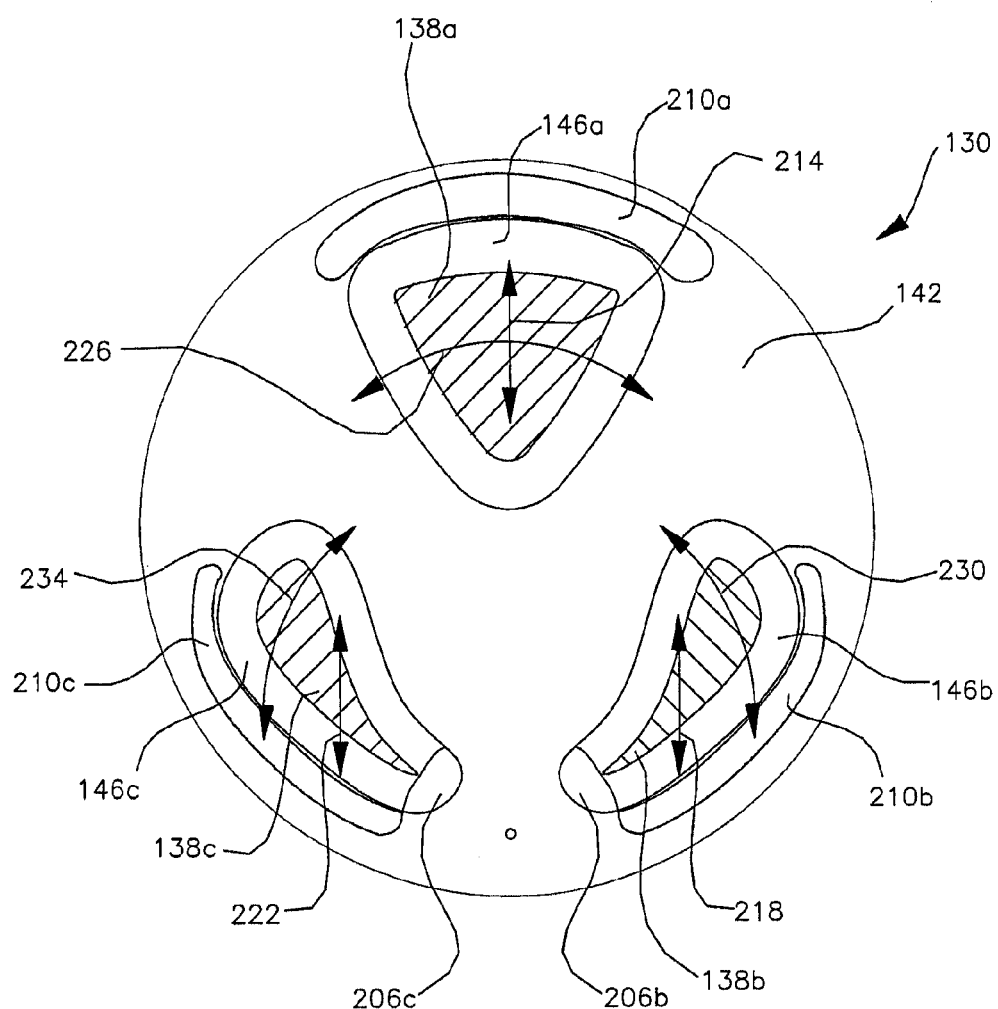
FIG. 18 shows another top view of the lower portion and projections of the upper portion of an artificial disc of the present invention.

The inner retaining walls 206 may be used to more precisely control the movement of the projections 138 and upper surface 134 in selected directions. FIG. 18 shows such a use. For example, inner retaining walls 206b, 206c may be placed on the inside sides of recesses 146b, 146c. The inner retaining walls 206b, 206c prevent movement of the lateral projections 138b, 138c in a purely lateral direction. The inner retaining walls 206b, 206c are positioned against the lateral projections 138b, 138c such that, in rotation, the lateral projections 138b 138c do not translate laterally but rotate about a point of contact between a lateral projection and inner retaining wall.

For example, if the upper portion 134 is rotated to the right, the lateral projections 138b, 138c can not simply translate to the left or right. The left lateral projection 138c may move forwards and to the right and the right lateral projection 138b may move backwards somewhat. The anterior projection 138a may move to the right and forwards. The left lateral projection 138c is raised vertically as it moves, as discussed previously. It is thus seen that the inner retaining walls 206b, 206c aid in constraining the movement of the artificial disc to imitate the movement of the natural spine. The inner retaining walls cause the center of rotation to be roughly between the retaining walls, closer to the posterior end of the artificial disc, where the center of rotation of the natural spine is located.

In forwards and backwards flexing/extending, the upper portion 134 should move as shown by arrows 214, 218, 222, in a manner similar to the natural spine. In rotation, the upper surface should move as shown by arrows 226, 230, 234, also in a manner similar to that of the natural spine.

It will be appreciated that it may not be possible to perfectly replicate the movement of the natural spine and still achieve an artificial disc 130 which is sufficiently stable. As such, the resulting design may be a compromise between matching the natural motion and providing inherent stability and self centering capabilities, for example. An artificial joint may also be a compromise which provides a good match to the natural motion, inherent stability, and which may be manufactured from a desired material without excessive expense or difficulty. The present invention, however, does provide a marked improvement over the inherently unstable artificial discs of the prior art and much more closely replicates the natural movements of the spine.

Figure 19:
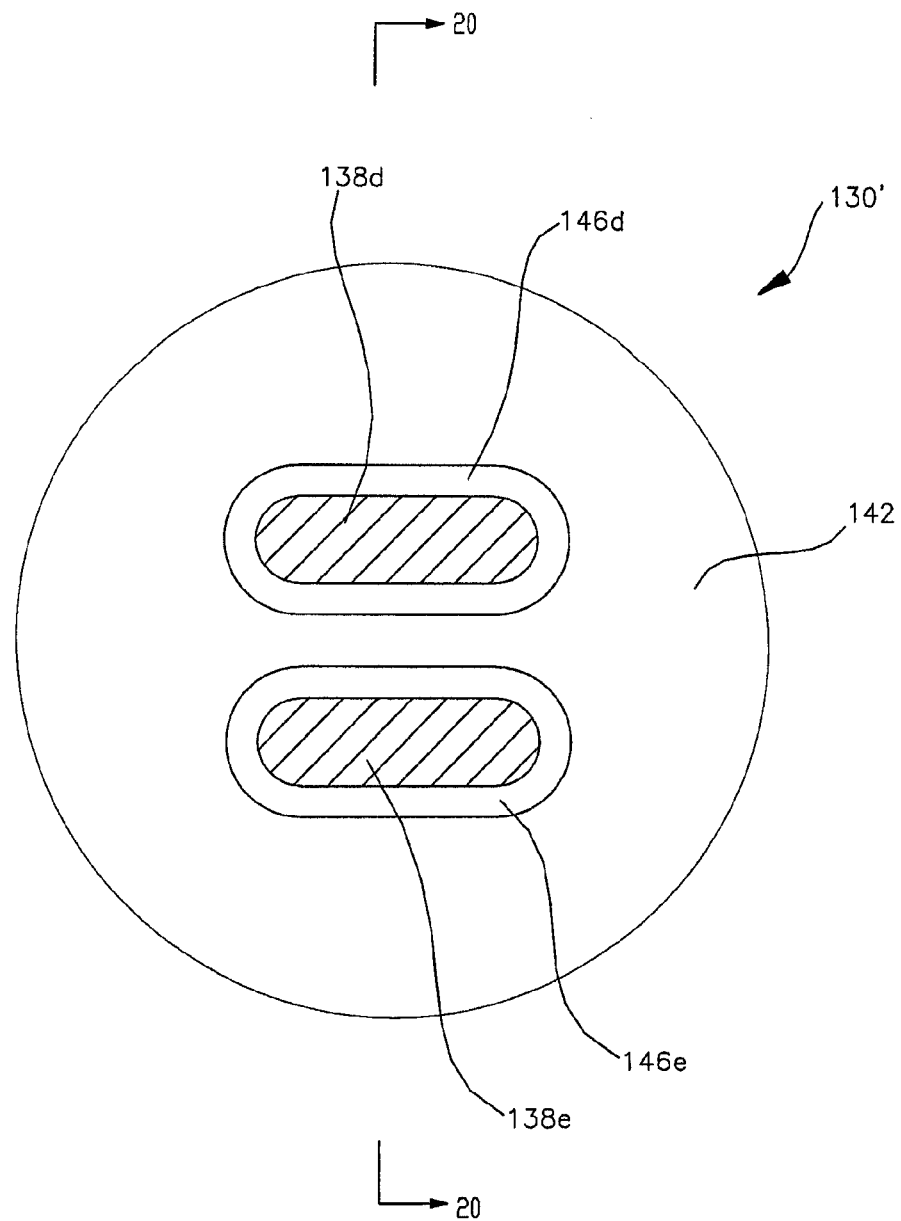
FIG. 19 shows another top view of an artificial disc of the present invention.

FIG. 19 shows another partially cut-away view of an artificial disc 130' of the present invention. The upper surface 134' (FIG. 20) includes an anterior projection 138d and a posterior projection 138e. The lower surface 142 includes an anterior recess 146d and a posterior recess 146e. While the two projection/recess design may not provide an artificial joint which is as stable as a three or more projection design, it still provides a marked improvement in stability and movement over a conventional artificial disc. For example, the elongate configuration of the projections 138d and 138e minimizes the effort necessary to center the joint compared to a hemispherical single projection as in the prior art.

Figure 20:
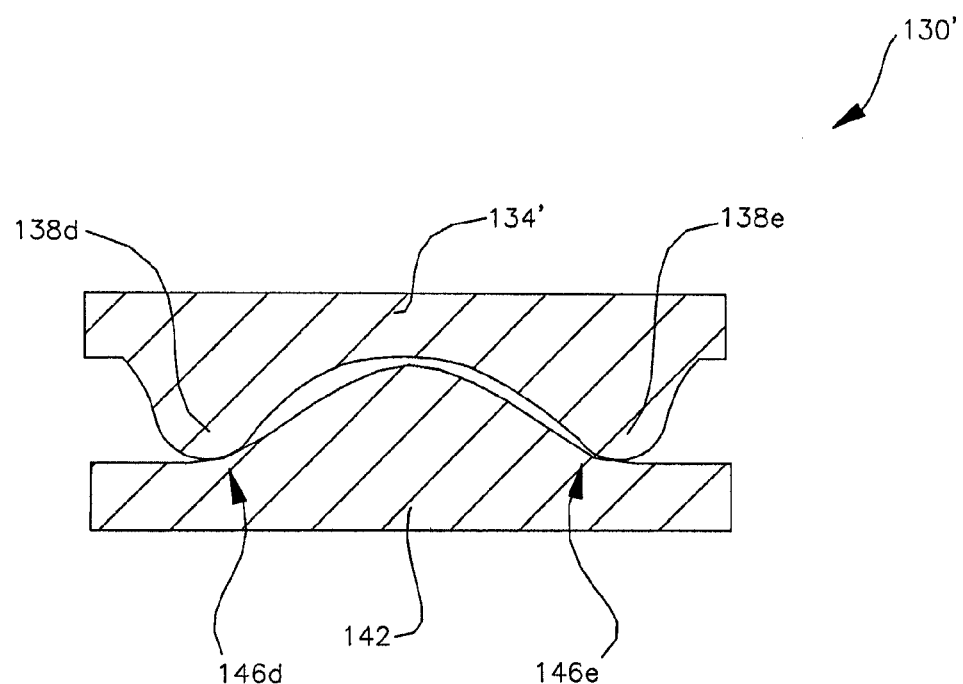
FIG. 20 shows a cross-sectional view of the artificial disc of FIG. 19 taken along line 20-20.

FIG. 20 shows a cross sectional view of the artificial disc 130' of FIG. 19 along line 20-20. The projections 138 and recesses 146 configured as shown will cause the anterior projection 138d to slide forwards (to the left) and the posterior projection to slide forwards and upwards during a forwards flexing of the artificial disc 130', tilting the upper portion 134' forwards and sliding the upper surface in a manner similar to the natural spine.

Similarly, the posterior projection 138e will slide backwards and the anterior projection 138d will slide backwards and upwards along the recesses 146 during a posterior extending of the artificial disc, tilting the upper portion 134' backwards and sliding the upper portion similar to the natural spine. The upward movement of the upper portion 134' during the forwards and backwards flexing/extending of the artificial disc will move the supported body against gravity, and cause gravity to bias the artificial disc back into a neutral position, as discussed above.

In rotation, the upper portion 134' will rotate roughly around the center of the artificial disc 130', and the upper disc will be raised slightly as the edges of the projections 138 contact the inclined portions of the recesses 146, causing gravity to bias the artificial disc 130' into a neutral position. By modifying the configuration of the projections and recesses, the upper portion 134' can be made to rotate about an axis other than at the center of the upper portion. Thus, an artificial joint may be provided which more accurately resembles the movement of the natural spine.

It will be appreciated that the two projection artificial disc 130' of FIGS. 19 and 20 may not approximate the movement of the natural spine quite as closely as the three projection artificial disc 130 of FIGS. 8 through 18, but it may be easier to manufacture. Furthermore, it remains more stable than the artificial joints of the prior art.

Figure 21:
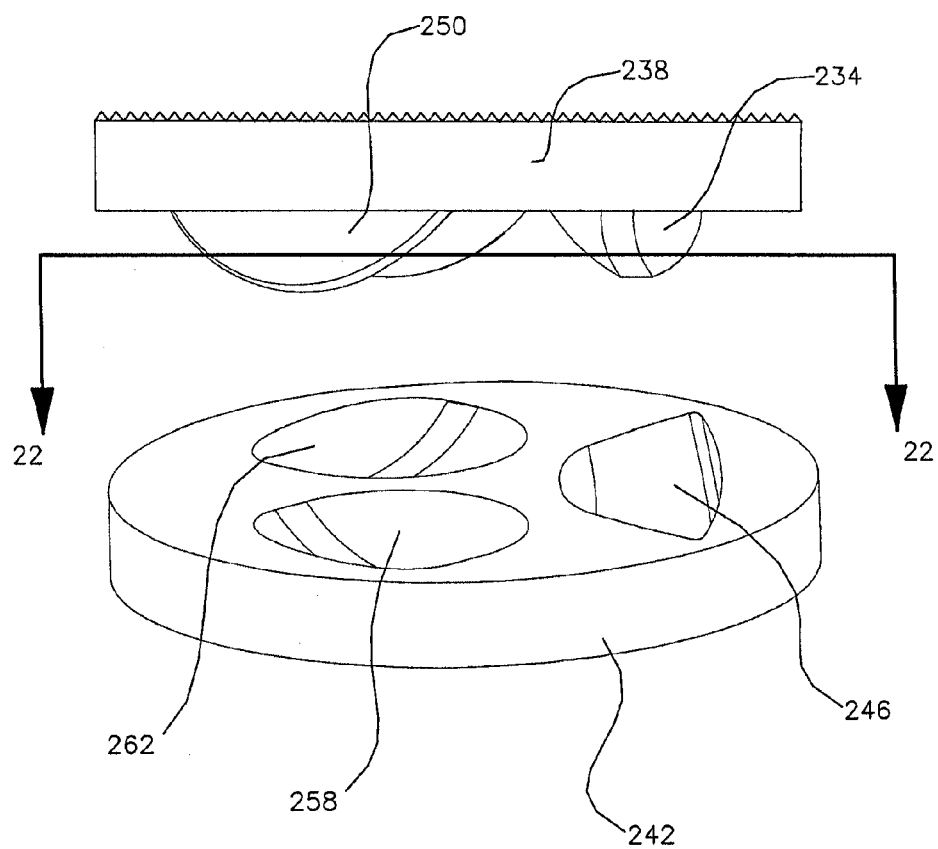
FIG. 21 shows a perspective view of an artificial joint of the present invention having differently shaped projections.

FIG. 21 shows a perspective view of another artificial disc which is similar to that of FIGS. 8-18 and functions in a similar manner. The disc is different in that the anterior projection 234, as formed on the top 238 of the joint, has a more abruptly terminated anterior side. The bottom 242 is formed with a recess 246 which has a corresponding shape. The lateral projections 250, (254 not shown) and lateral recesses 258, 262 may be formed with similar shapes as that of projection 234 and recess 246, or may be more smoothly shaped as shown previously.

Figure 22:
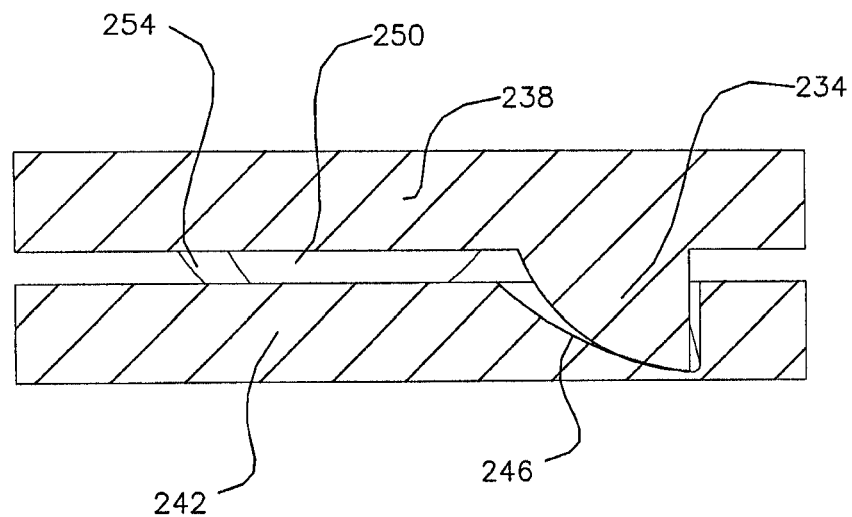
FIG. 22 shows a cross-sectional view of the artificial joint of FIG. 21 taken along line 22-22 of FIG. 21.

FIG. 22 shows a cross-sectional view of the joint of FIG. 21 taken along line 22-22. It can be seen how the nearly vertical anterior side of projection 234 and the nearly vertical anterior side of the recess 246 will prevent the upper portion 238 from moving more than a short distance to the right relative to the lower portion 242, providing a motion limit. Providing such a motion limit helps ensure that the artificial joint is not hyper-extended once installed into a patient. As has been discussed previously, the recess 246 may be shaped such that the projection 234 will move relatively horizontally when moving to the right from the neutral position shown, and such that the projection moves vertically as well as to the left when moving to the left relative to the base and from the neutral position shown. As has been discussed, this creates a stable joint wherein compressive forces on the joint bias the joint into a neutral position. It will be appreciated that one or more of the projections and recesses may be formed in such a manner to thereby limit the motion of the joint. One or more of the different methods of limiting the motion of the artificial joint discussed herein may be used with any of the different joint configurations shown herein.

Figure 23:
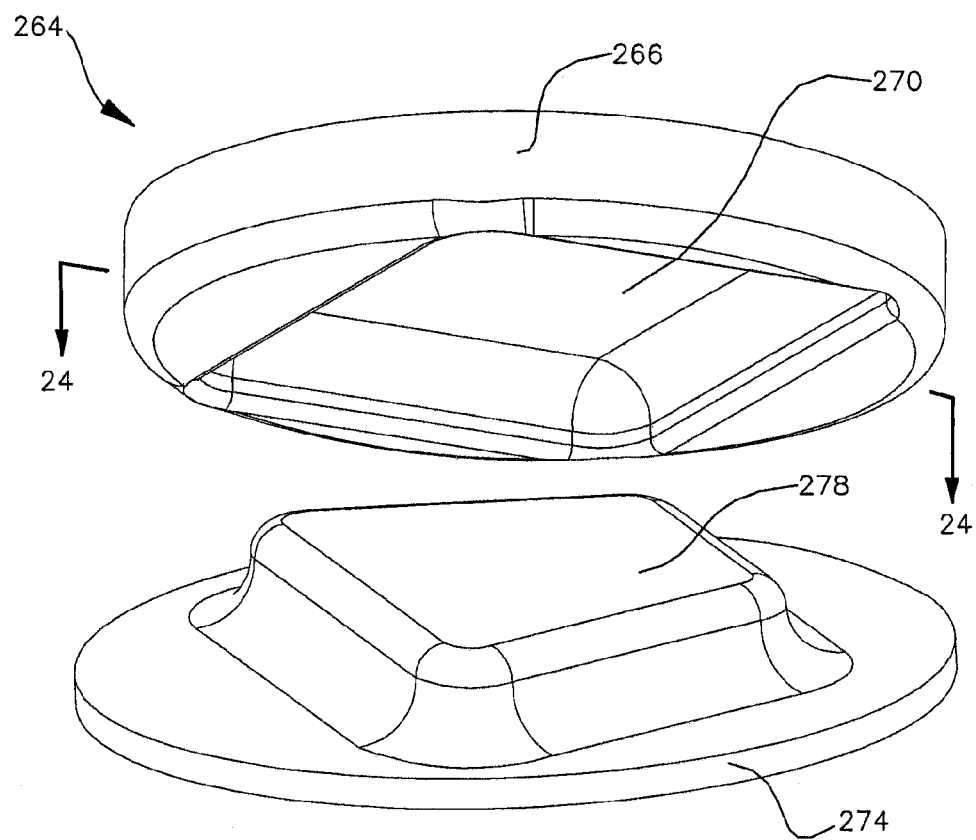
FIG. 23 shows a perspective view of another artificial joint of the present invention.

FIG. 23 shows another artificial disc 264 which uses a single projection and a single recess to achieve the stability and motion control discussed herein. The top 266 includes a single recess 270, and the bottom 274 includes a single projection 278. The recess 270 and projection 278 are formed with rounded and/or angled engaging surfaces so as to provide for smooth motion therebetween. The projection 278 and recess 270 may be formed as polygonal shapes or other shapes to limit the rotation of the artificial joint and provide more natural motion of the joint. It will be appreciated that a circular lobe 278 and recess 270 will not limit the rotation of the top 266 relative to the bottom 274 of the joint. The projection 278 and recess 270 may be formed as ovals, squares, triangles, or other shapes.

Figure 24:
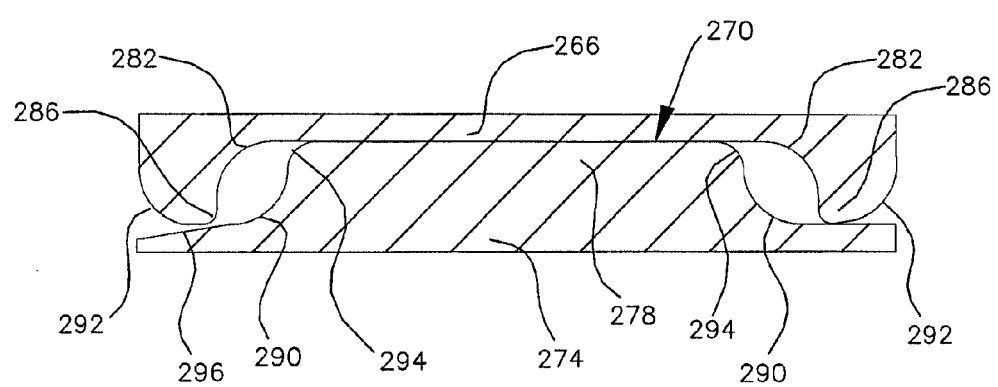
FIG. 24 shows a cross-sectional view of the artificial joint of FIG. 23 taken along line 24-24 of FIG. 23.

FIG. 24 shows a cross sectional view of the artificial disc 264. It can be seen how the recess 270 includes sloping outer wall 282 which transition from the center of the recess and rounded shoulders 286, and how the projection 278 also has a sloping transitional region 290 and rounded shoulders 294. The shoulder 294 of the projection contacts and slides across the sloping outer wall 282, and the shoulder 286 of the recess 270 contacts and slides across the sloping transition region 290 of the projection.

In viewing the artificial joint 264, it can be appreciated that if the top 266 is moved to the right relative to the bottom 272, the right side of the top will move generally horizontally across the generally horizontal surfaces, and the left side of the top will be raised as the shoulders 286, 294 engage and move across the sloping transition regions 282, 290. This will be the case for lateral bending or flexion/extension of the artificial joint 264. Thus, the artificial joint 264, while not perfectly approximating the natural motion of the spine, will create a similar motion and will create a joint which is biased into the neutral position shown by compressive forces applied to the joint (as is the case when a joint is installed in a human spine). In order to better control the motion of the artificial joint 164, the upper portion 266 may be curved away from the contact points on the shoulders 286 as indicated at 292. Additionally, the lower portion 274 may slope downwardly in the posterior portion as indicated at 296 so as to more closely approximate the natural motion of the spine.

Figure 25:
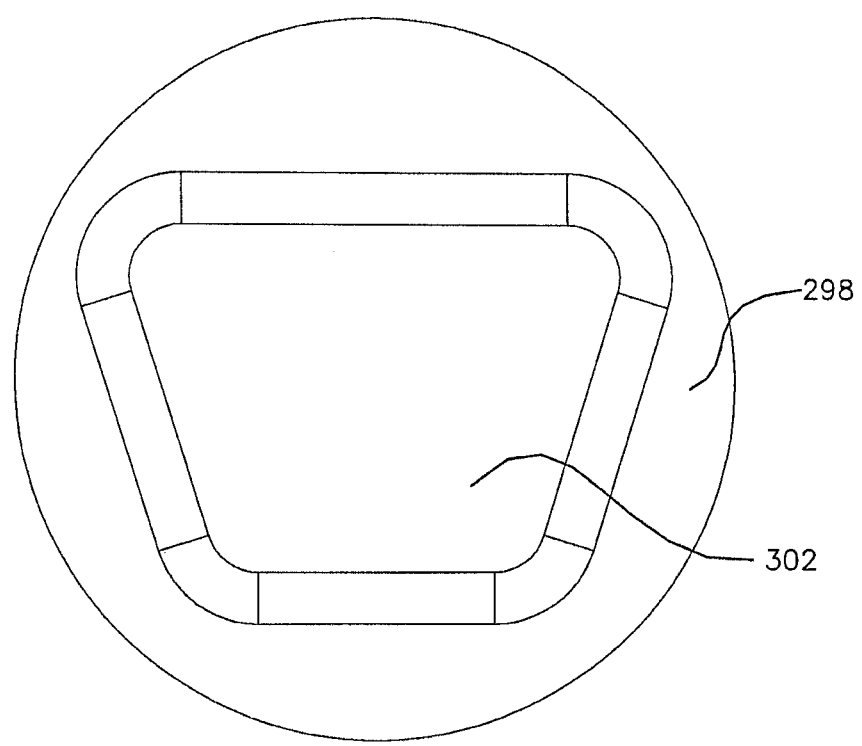
FIG. 25 illustrates another artificial joint of the present invention.

FIG. 25 shows a bottom view of a top portion 298 of an artificial joint similar to that shown in FIGS. 23 and 24. It can be seen how the recess 302 (and the corresponding projection formed on the bottom of the joint) may be formed in shapes other than a square or rectangular shape as shown previously. Different shapes of projections and recesses will alter the characteristic motion of the resulting joint. For example, a projection/recess shaped as shown may tend to lift more when moving in one direction than in the opposite direction or provide different rotational characteristics during rotation or lateral bending of the joint. Thus, a shape may be selected which reasonably approximates the motion of the natural spine and creates a joint which is biased into a neutral position by compressive forces, but which is also a relatively simple shape to manufacture.

Figure 26:
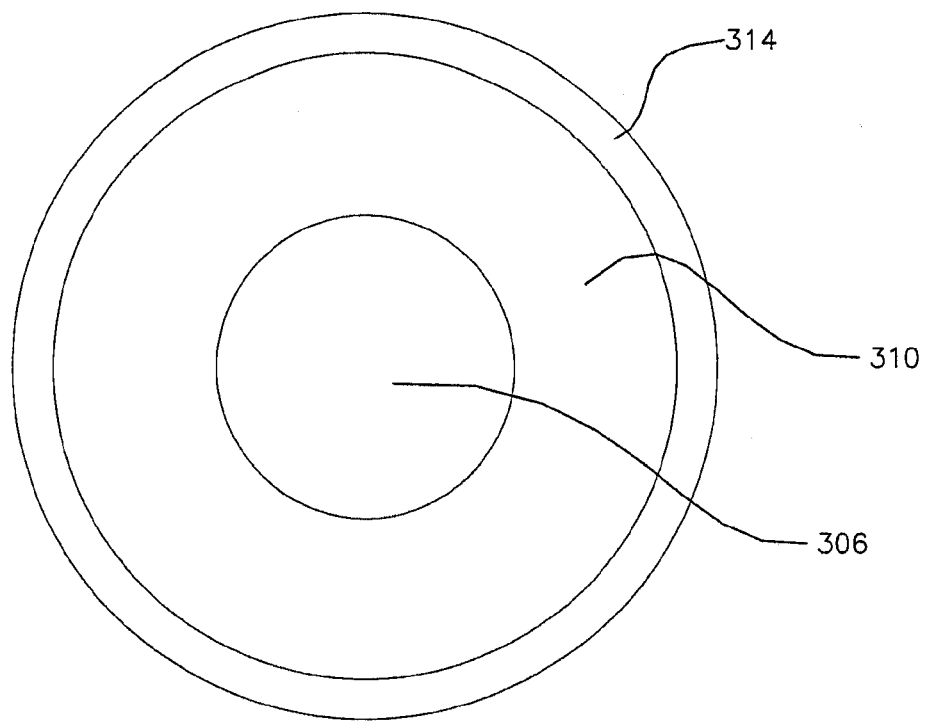
FIG. 26 shows an artificial joint of the present invention used as a disc nucleus replacement.

FIG. 26 illustrates the use of an artificial joint 306 of the present invention used to replace the nucleus of a damaged spinal disc, while leaving the annulus 310 (annulus fibrosis) of the natural disc in place. Leaving the annulus 310 as intact as is possible may be advantageous in some cases as it provides support to the artificial joint 306, helping to keep the joint 306 centered over the vertebra 314 or helping to keep the top of the joint centered over the bottom of the joint. An artificial joint which is used for a nuclear replacement will typically be smaller than a joint used for a total disc replacement. Any of the joint designs shown above may be used as either a total disc replacement or a nuclear replacement if manufactured in the appropriate size and configuration and made of an appropriate material.

Figure 27:
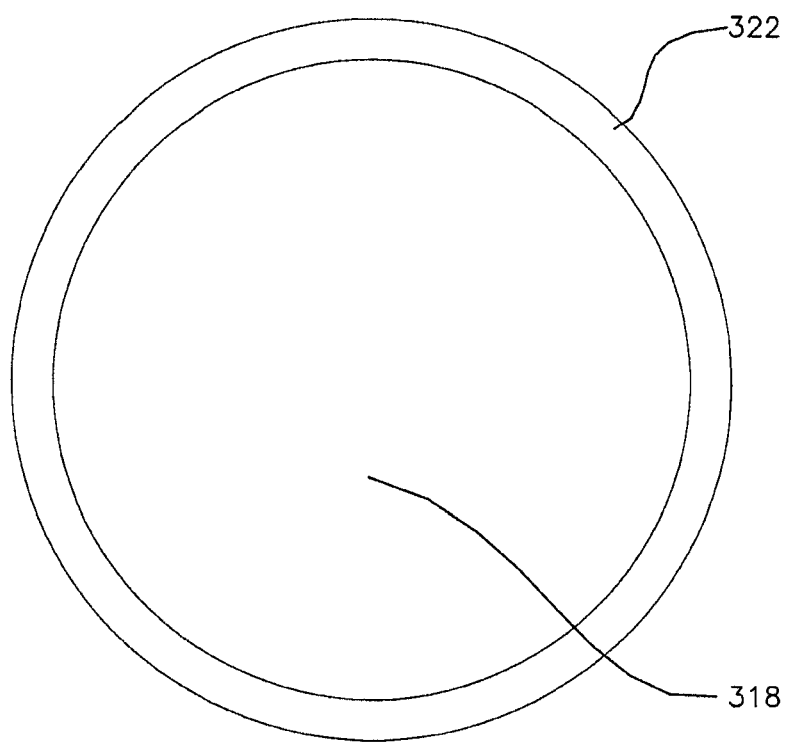
FIG. 27 shows an artificial joint having a restraining band according to the present invention.

FIG. 27 illustrates an artificial disc 318 with an elastomeric band 322 surrounding the joint 318. The band 322 may aid in loosely constraining the motion of the joint and in keeping the top of the joint centered above the bottom of the joint. Any of the above joint designs may incorporate such a band 322 if desired.

Figure 28:
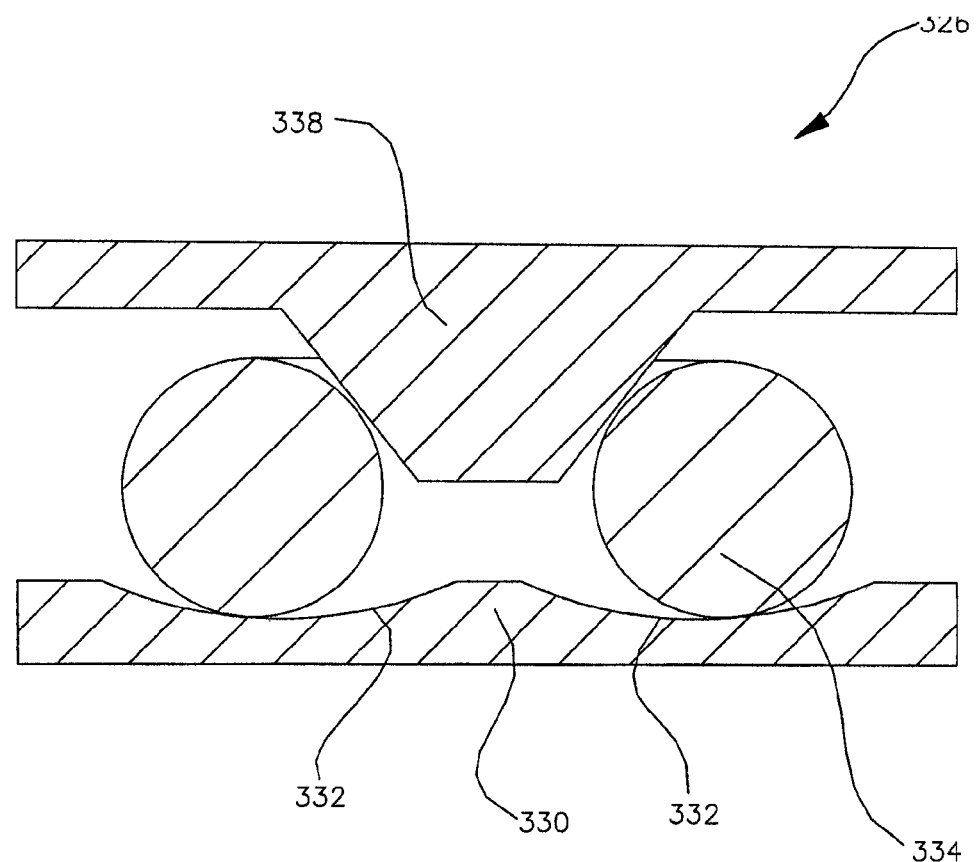
FIG. 28 shows a cross-sectional view of another artificial joint of the present invention.

FIG. 28 illustrates an alternate artificial disc according to the present invention. The artificial joint 326 includes a base portion 330 having a circular recess 332 formed therein, a toroid 334, and a top 338 which includes a conical or frusto-conical portion that nests in the toroid 334. The toroid 334 can translate across the base 330 but is biased into the center of the base by compressive forces. The top 338 may pivot inside of the toroid 334 and is elevated as it pivots because of the interaction between the conical portion and the toroid.

Figure 29:
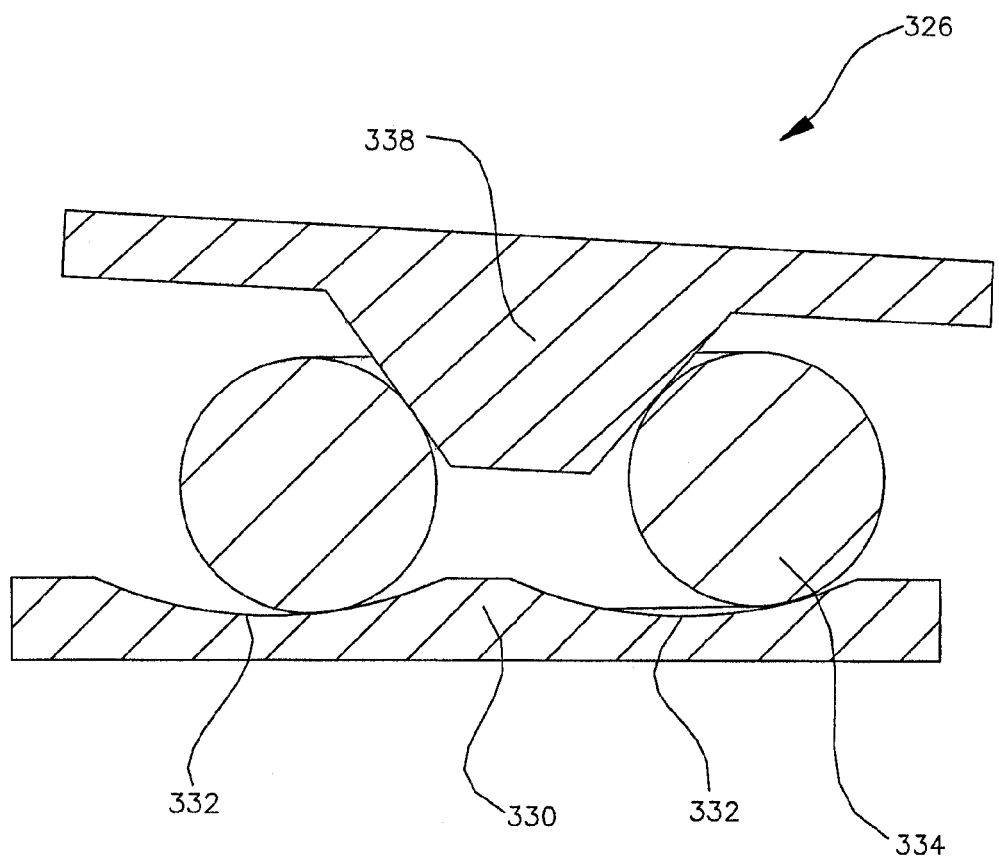
FIG. 29 shows another cross-sectional view of the joint of FIG. 28.

FIG. 29 illustrates the joint of FIG. 28 in a position corresponding to a flexion/extension or lateral bending motion. It can be seen how the toroid 334 is elevated as it slides across the recess 332 in the base 330, and how the top 338 is elevated as it pivots. The joint 326 utilizes symmetrical shapes which may be relatively easy to manufacture and roughly approximates the natural spinal motion. The flexion/extension and lateral bending of the joint closely approximate the natural spine, and are also biased into a neutral position. While the rotation is unconstrained, this motion may be the easiest for the muscles and surrounding tissue to control and is the least affected by the compressive forces placed on the natural spine.

Figure 30:
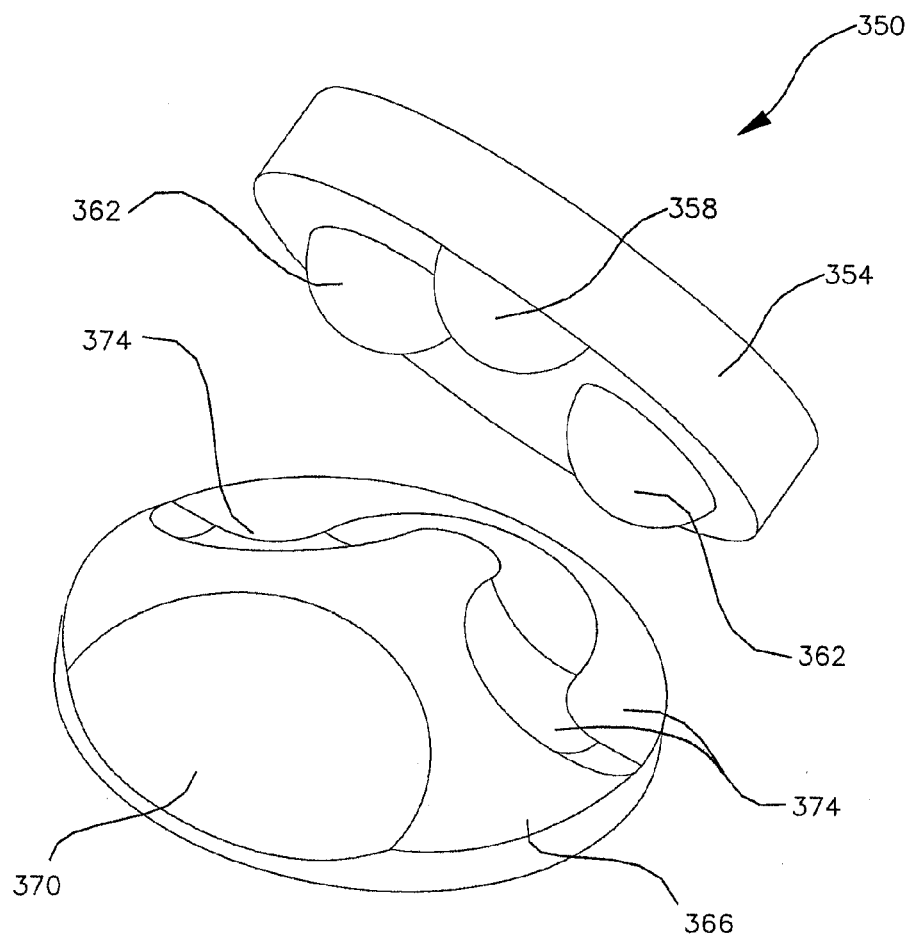
FIG. 30 shows an exploded perspective view of a artificial joint similar to that of FIGS. 8-18.

Turning now to FIG. 30, an exploded perspective view of another artificial joint is shown. The joint, indicated generally at 350, is similar to the artificial joints shown in FIGS. 8-22. The joint 350 includes an upper portion 354 having an anterior projection 358 and two lateral projections 362. The joint 350 also includes a lower portion 366 which includes an anterior recess 370 and two lateral recesses 374, which may be connected together into a single recess as is shown. It will be appreciated, however, that the narrow connecting portion as shown does not contribute to the motion of the artificial disc and is a manufacturing convenience. The joint functions as has been discussed previously with respect to FIGS. 8 through 18. That is to say that the upper portion 354 slides across the lower portion 366 allowing anterior-posterior, lateral, and rotating translational movements. As the upper portion 354 slides across the lower portion 366, the projections 358, 362 are also typically moved vertically relative to the lower portion 366 due to the curved surfaces of the recesses 370, 374. As will be shown in the following figures, the projections 358, 362 are generally spherical and the recesses 370, 374 have circular vertical cross sections. This results in an artificial joint 350 which closely matches the natural motion of the spine and provides inherent stability as discussed above but which is easier to manufacture.

Similar to the artificial joints of FIGS. 8-22, the projections 358, 362 are moved upwardly relative to the lower portion 366 as they move towards the center of the lower portion. This vertical movement results in a net expansion of the artificial joint, and thus results in a joint where compressive forces applied to the joint bias the joint back towards a neutral position. This vertical motion also results in a joint which provides motion that more closely matches the natural kinematic motion of the human spine. It will be appreciated that the slopes and changes of curvature in the recesses 370, 374 may be adjusted to control the amount of vertical movement generated by a particular horizontal movement.

FIGS. 31 through 34 show additional details of the upper portion 354 of the joint 350 of FIG. 30. FIG. 31 is a bottom view of the upper portion 354. FIGS. 32 and 33 are cross sectional views taken along section lines 32 and 33 of FIG.

31. FIG. 34 is a perspective view of the upper portion 354. One advantage of the joint 350 is that it uses a somewhat simpler and more uniform surface shape and geometry than the joints of FIG. 11 while achieving a motion which closely replicates the motion of the natural spine. The upper portion may be formed as a substantially flat disc with semi-spherical projections 358, 362. The semi-spherical projections 358, 362 are more easily shaped and polished that the more complex projections such as are shown in FIG. 11, for example.

Figure 35:
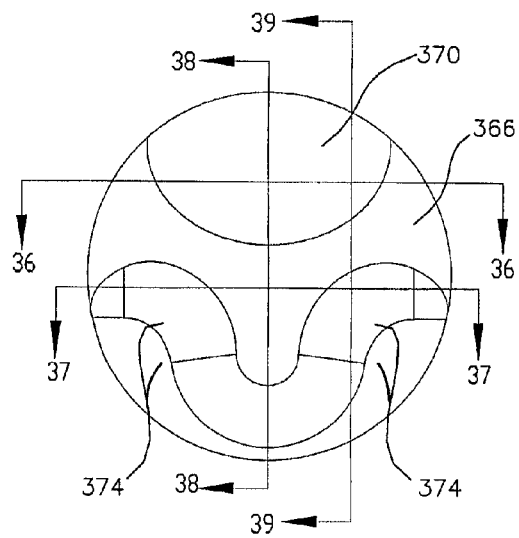
FIG. 35 shows a top view of the lower portion of the joint of FIG. 30.
Figure 38:
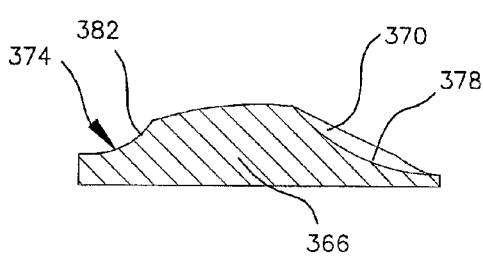
FIG. 36 through 39 show cross sectional views of the lower portion of the joint of FIG. 30 taken along section lines 36 through 39 of FIG. 35.
Figure 36:
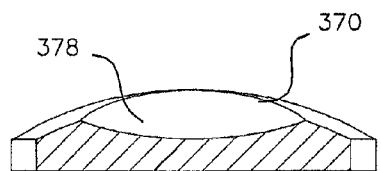
Figure 39:
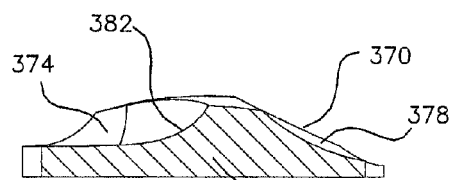
Figure 40:
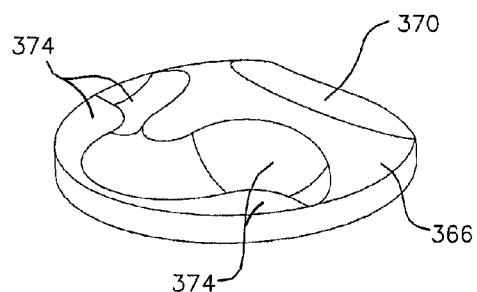
FIG. 40 shows a perspective view of the lower portion of the joint of FIG. 30.

FIGS. 35 through 40 show additional details of the lower portion 366 of the joint 350 of FIG. 30. FIG. 35 shows a top view of the lower portion 366 and FIGS. 36 through 39 are cross sectional views of FIG. 35 taken along section lines 36-39, respectively. FIG. 40 is a perspective view of the lower portion 366. As can be seen in FIGS. 30 and 35 through 40, the two lateral recesses 374 may be connected together across the back lower portion 366 of the artificial joint. While the lateral projections 362 may never move fully to the back of the lower portion 366 directly between the lateral recesses 374, it may be easier to form and polish the joint with such a configuration.

It can be observed from FIGS. 36 through 39 that the contact surface 378 of the anterior recess 370 (across which anterior projection 358 slides during articulation of the joint) is gently curved and sloped. The contact surface 378 of recess 370 allows the projection 358 to move downwardly as is slides away from the center of the lower portion 366 and upwardly as it slides towards the center of the lower portion, such as during flexion and extension of the joint, as well as upwardly as it moves laterally across the lower portion, such as during rotation of the joint. The curvature of the contact surface 370 results in greater vertical movement per unit of horizontal movement when the projection 358 is closer to the center of the lower portion 366 as compared to when the projection 358 is closer to the outer edge of the lower portion.

Figure 37:
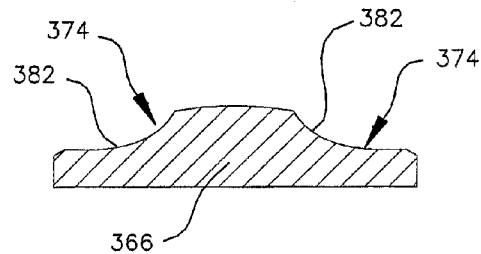

In order to facilitate easier manufacture of the lower portion 366, the recesses 370, 374 may each have a circular vertical cross section as is visible in FIGS. 37 through 39. This allows a circular grinding or polishing tool to be swept across the lower portion during manufacture in order to form the recesses.

It can be observed from FIGS. 36-39 that the contact surfaces 382 of the lateral recesses 374 have smaller radii of curvature than that of contact surface 378 of anterior recess 370. As such, the contact surfaces 382 of the lateral recesses 374 are horizontal or nearly horizontal near the outer edges of the lower portion 366 and more steeply sloped near the center of the lower portion. As a result, the lateral projections 362 experience little or no vertical movement as they move across the surface 382 away from the center of the lower portion 366 and move upwardly away from the lower portion 366 of the joint as they move towards the center of the lower portion. The curvature of the contact surfaces 382 is such that the vertical movement of the lateral projections 362 is greater per unit of horizontal movement when the lateral projections are closer to the center of the lower portion 366.

The steeper slope of the more central portions of contact surfaces 382 as compared to contact surface 378 provides a net restoring force which biases the artificial joint 350 to a neutral position (i.e. an un-displaced position). Thus, the slope of contact surface 378 will tend to bias the anterior projection 358 away from the center of the lower portion even in a neutral position, but the greater slopes of the lateral contact surfaces 382 will provide a greater bias against further anterior displacement to the lateral projections 362 and maintain the joint in a neutral position while compression is applied to the artificial joint 350.

The shapes and curvatures of the contact surfaces 378, 382 of the recesses 370, 374 results in a kinematic movement of the artificial joint 350 which approximates that of the natural spine and which also tends to return the artificial joint 350 to a neutral position when the joint 350 is placed under compression. A neutral position is where the upper portion is aligned over the lower portion and not displaced from the center thereof. (It will be appreciated that upper or lower portions may have a base which is shifted somewhat from the projections so that the upper and lower base portions are somewhat misaligned even though the projections and recesses are in a neutral orientation. Such is within the scope of the invention.) In use, the artificial joint 350 will be biased towards an un-displaced, neutral position by the compressive forces placed upon the joint by the body and will therefore stabilize the joint. The artificial joint 350 presents a good approximation of the natural movement of the spine, i.e. the rotation and translation which occurs with lateral bending or rotation of the spine and the translation which occurs with flexion and extension of the spine.

Turning now to FIGS. 41 through 53, another artificial spinal joint 386 of the present invention is shown. The artificial joint 386 operates according to the principles discussed above in that the artificial joint provides a motion that closely matches the natural motion of the spine and which is inherently stable. The joint 386 is stable in that the joint experiences a net expansion as a result of the intended ranges of motion and thus the compressive forces placed on the joint while in a spine will tend to restore the joint to a neutral, unbiased position.

Figure 41:
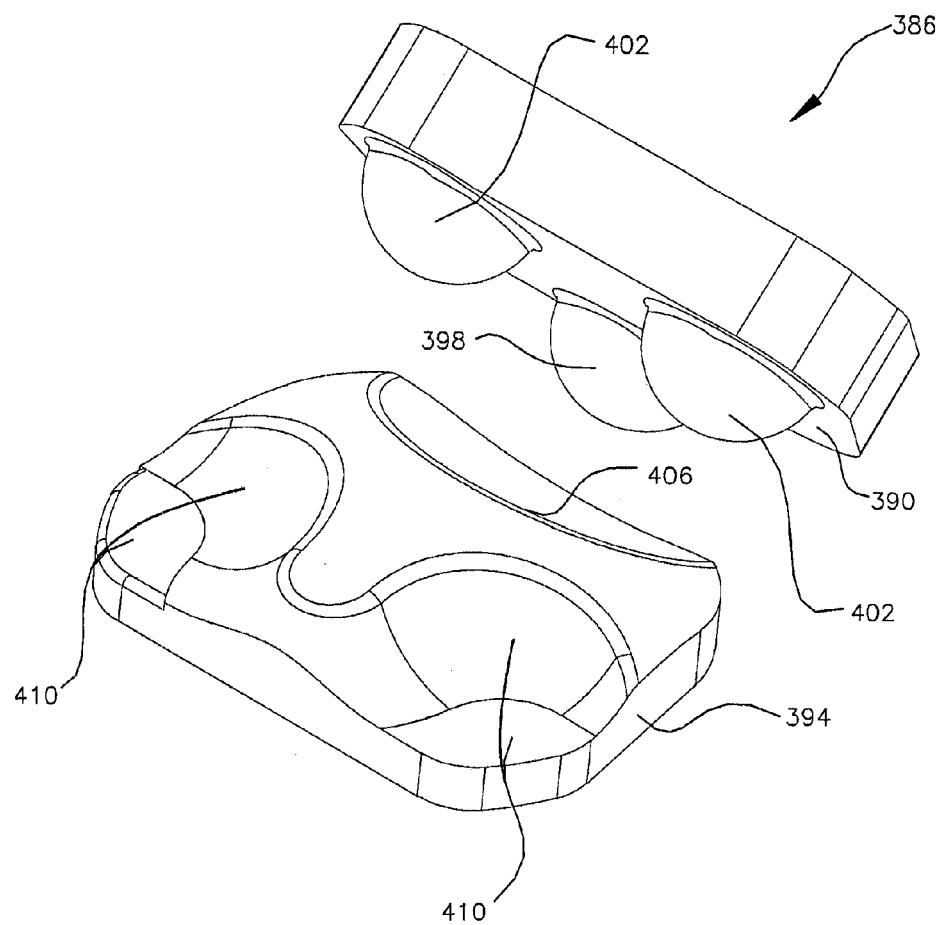
FIG. 41 shows an exploded perspective view of an artificial joint similar to that of FIGS. 8-18, and 30-40.
Figure 43:
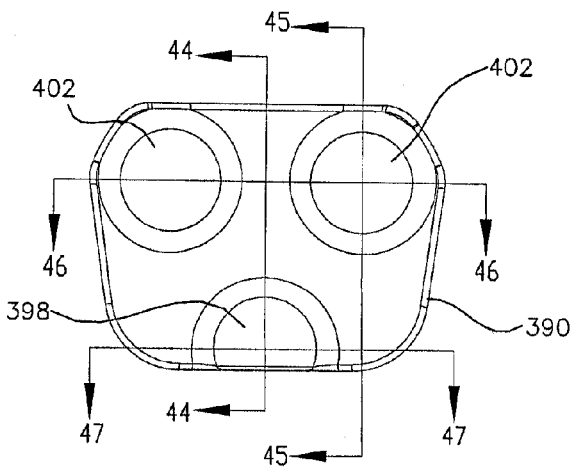
FIG. 43 shows a bottom view of the upper portion of the joint of FIG. 41.
Figure 42:
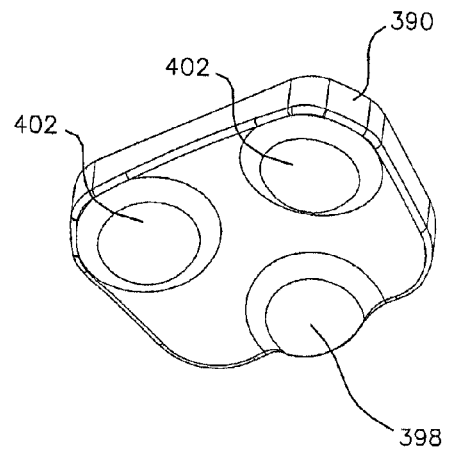
FIG. 42 shows a bottom perspective view of the upper portion of the joint of FIG. 41.
Figure 46:
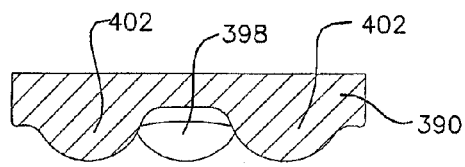
FIG. 44 through 47 show cross sectional views of the upper portion of the joint of FIG. 41 taken along section lines 44 through 47 of FIG. 43.
Figure 44:
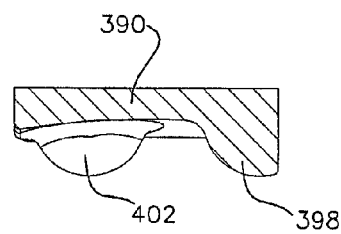
Figure 47:
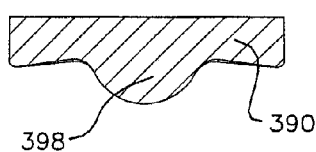
Figure 45:
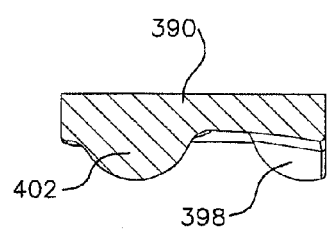

FIGS. 42 through 46 show the upper portion 390 of the joint 386 of FIG. 41 while FIGS. 48 through 53 shows the lower portion 394 of the joint. FIG. 42 shows a perspective view of the upper portion 390. FIG. 43 shows a bottom view of the upper portion 390 and FIGS. 44 through 47 show cross sectional views of the upper portion taken along section lines 44 through 47 of FIG. 43. Similarly, FIG. 48 shows a perspective view of the lower portion 394 while FIG. 49 shows a top view of the lower portion 394 and FIGS. 50 through 53 shows cross sectional views of the lower portion taken along section lines 50 through 53 of FIG. 49.

The joint 386 differs from the joints discussed above in FIGS. 8 through 18 and 30 through 40 in that it contains a single posterior projection 398 and posterior recess 406 and two anterior lateral projections 402 and two anterior lateral recesses 410. Otherwise, the upper portion 390 and lower portion 394 mate together in a similar manner and function in a similar manner to that discussed above.

The joint 386 includes two anterior projections 402 and a single posterior projection 398 and corresponding recesses so as to better utilize the stabilizing effects of the facet joints (52 of FIG. 3). During forward flexion of the joint 386, more pressure is placed on the two anterior projections 402 and anterior recesses 410, providing greater lateral stability. During backwards extension of the joint 386, more pressure is placed on the single posterior projection 398 and posterior recess 406 which results is somewhat less lateral stability than is provided in forward flexion of the joint. However, the facet joints 52, which are found on the posterior of the spine, provide additional lateral stability during extension of the joint 386. Thus, the two lateral projections 402 and recesses 410 are better utilized on the anterior of the joint 386.

Otherwise, the joint 386 of FIGS. 41 through 53 is similar to the joint 350 of FIGS. 30 through 40. As illustrated in FIGS. 44 through 47, the projections 398, 402 have spherical shapes to allow for easier grinding and polishing of the upper portion 390 when a material such as polycrystalline diamond (PDC) is used. The recesses have circular vertical cross sections as illustrated in FIGS. 50 through 53 so as to allow for easier grinding and polishing with a circular rotary tool when using PDC or a similar material. The rotary tool may be swept through a relatively simple horizontal motion to grind the recess shapes shown. The joint 386 has been cut to a trapezoidal shape as such a shape closely matches the available space in the spine for total disc replacement. It will be appreciated that all of the preceding inventive artificial joints, while shown round for ease in drawing and discussing the joints, may be formed in a generally trapezoidal or generally rectangular shape as shown so as to most efficiently interface with the vertebral bodies.

Figure 54:
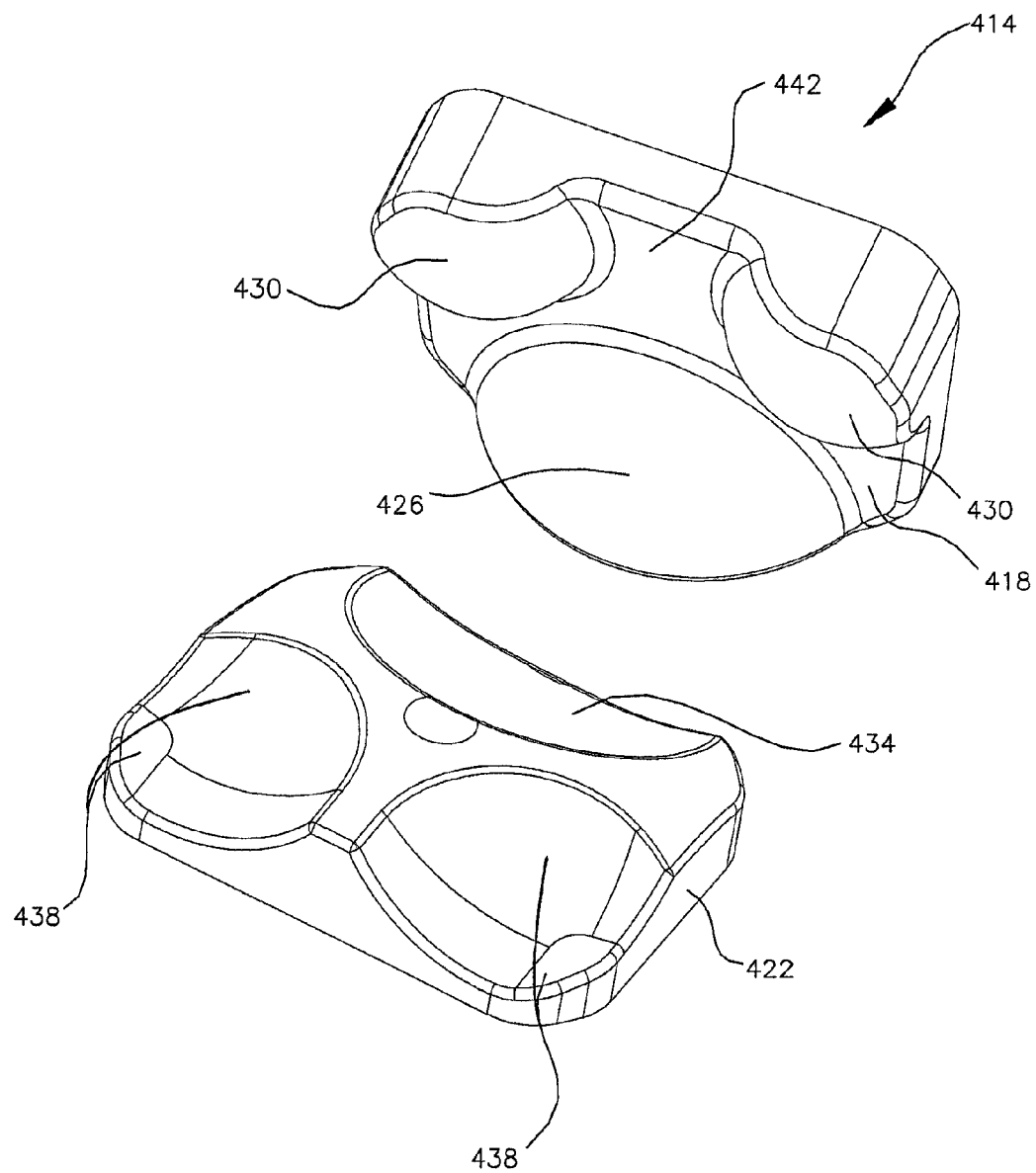
FIG. 54 shows an exploded perspective view of an artificial joint similar to that of FIGS. 8-18, 30-40, and 41-53.
Figure 56:
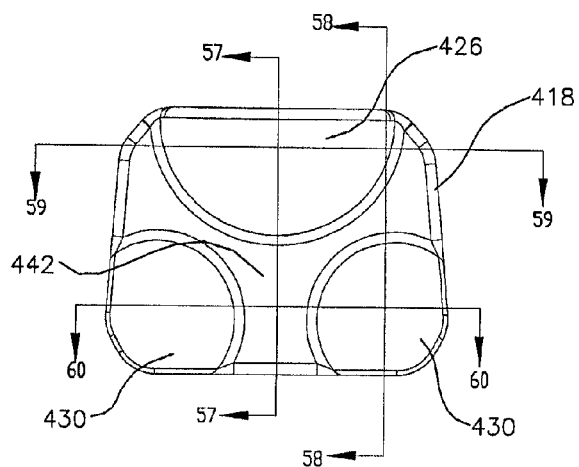
FIG. 56 shows a bottom view of the upper portion of the joint of FIG. 54.
Figure 55:
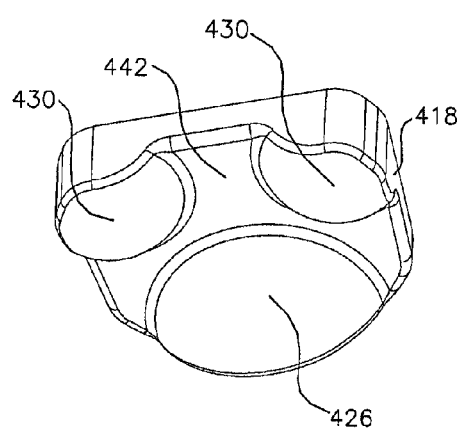
FIG. 55 shows a bottom perspective view of the upper portion of the joint of FIG. 54.
Figure 59:
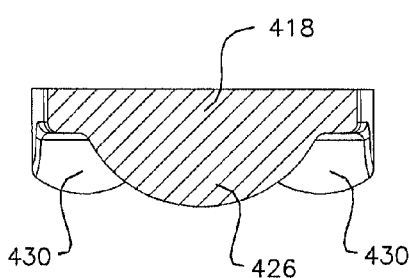
FIG. 57 through 60 show cross sectional views of the upper portion of the joint of FIG. 54 taken along section lines 57 through 60 of FIG. 56.
Figure 57:
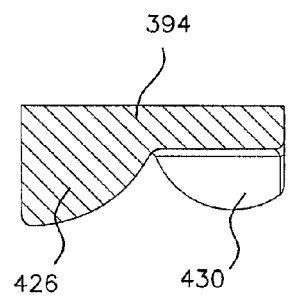
Figure 60:
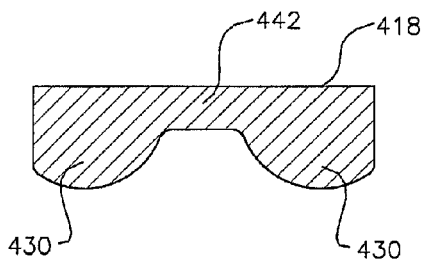
Figure 58:
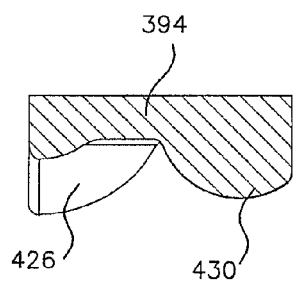
Figure 62:
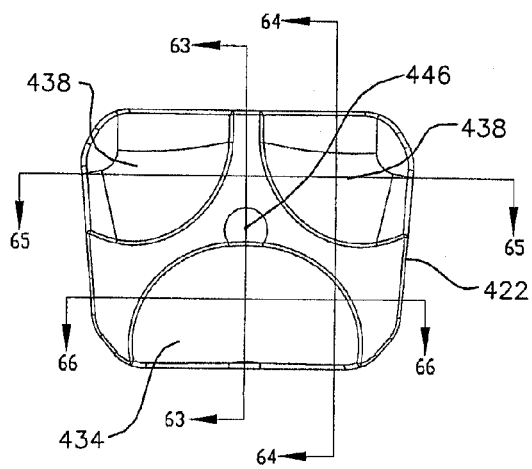
FIG. 62 shows a top view of the lower portion of the joint of FIG. 54.
Figure 61:
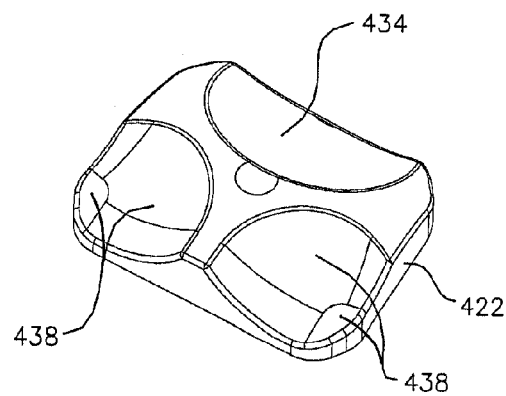
FIG. 61 shows a perspective view of the lower portion of the joint of FIG. 54.
Figure 65:
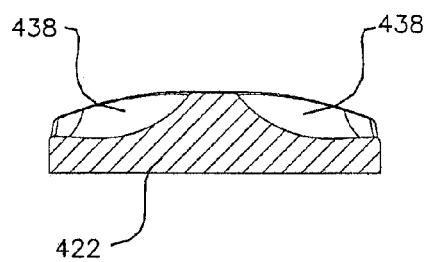
FIG. 63 through 66 show cross sectional views of the lower portion of the joint of FIG. 54 taken along section lines 63 through 66 of FIG. 62.
Figure 63:
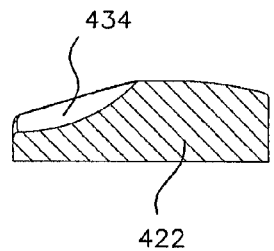
Figure 66:
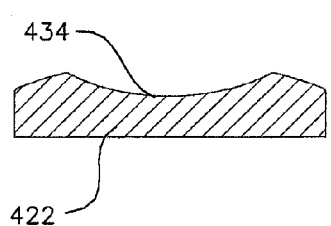

Turning now to FIGS. 54 through 66, another artificial spinal joint of the present invention is shown. FIG. 54 shows a perspective view of the joint 414. FIGS. 55 through 60 show the upper portion 418 of the joint 414 while FIGS. 61 through 66 show the lower portion 422 of the joint 414. FIG. 55 shows a perspective view of the upper portion 418. FIG. 56 shows a bottom view of the upper portion 418 and FIGS. 57 through 60 show cross sectional views of the upper portion taken along section lines 57 through 60 of FIG. 56. Similarly, FIG. 61 shows a perspective view of the lower portion 422 while FIG. 62 shows a top view of the lower portion 422 and FIGS. 63 through 66 shows cross sectional views of the lower portion taken along section lines 63 through 66 of FIG. 62.

The joint 414 is similar to the joint 386 discussed above in that it contains a single posterior projection 426 and posterior recess 434 and two anterior lateral projections 430 and two anterior lateral recesses 438. The joint 414 is different in that the projections 426, 430 and recesses 434, 438 are larger that those of the joint 386 so as to further lower the contact pressure of the joint and further reduce the stress placed on the material used to construct the joint.

The projections 426, 430 are spherical in shape and the recesses 434, 438 have circular vertical cross sections so as to allow for simplified grinding and polishing as discussed above, and provide the desired motion as described in the present application to closely match the natural motion of the spine. In order to maximize the stability of the joint 414, the projections 426, 430 and recesses 434, 438 have been moved close to the edges of the upper portion 418 and lower portion 422 while still maintaining a desired range of motion. This increases the 'footprint' of the contact points and maximizes the forces which tend to restore the joint to a neutral position when the joint is compressed.

By way of example, the following dimensions have been found to produce a suitable artificial joint for total disc replacement of cervical spine discs. The upper portion 418 and lower portion 422 are about 15.5 mm wide and about 11.9 mm long (front to back). The relatively flat base 442 of the upper portion 418 (extending between the projections 426, 430) is approximately 1.9 mm thick. On the upper portion 418, the posterior projection 426 is approximately 11.2 mm in diameter, and has a center which is located along the lateral centerline, and positioned about 1.7 mm from the posterior edge of the upper portion. The posterior projection 426 is placed such that it extends approximately 3.6 mm from the base portion 442, to a total combined thickness of about 5.5 mm.

The two anterior lateral projections 430 are approximately 6.9 mm in diameter, and have centers which are located about 7.2 mm in front of the center of the posterior projection 426 and laterally about 5.35 mm from the lateral centerline of the upper portion 418. The anterior lateral projections 430 extend about 2.9 mm from the base portion 442, to a total combined thickness of about 4.8 mm. Section lines 57 through 60 on FIG. 56 pass through the centers of the projections 426, 430.

Figure 67:
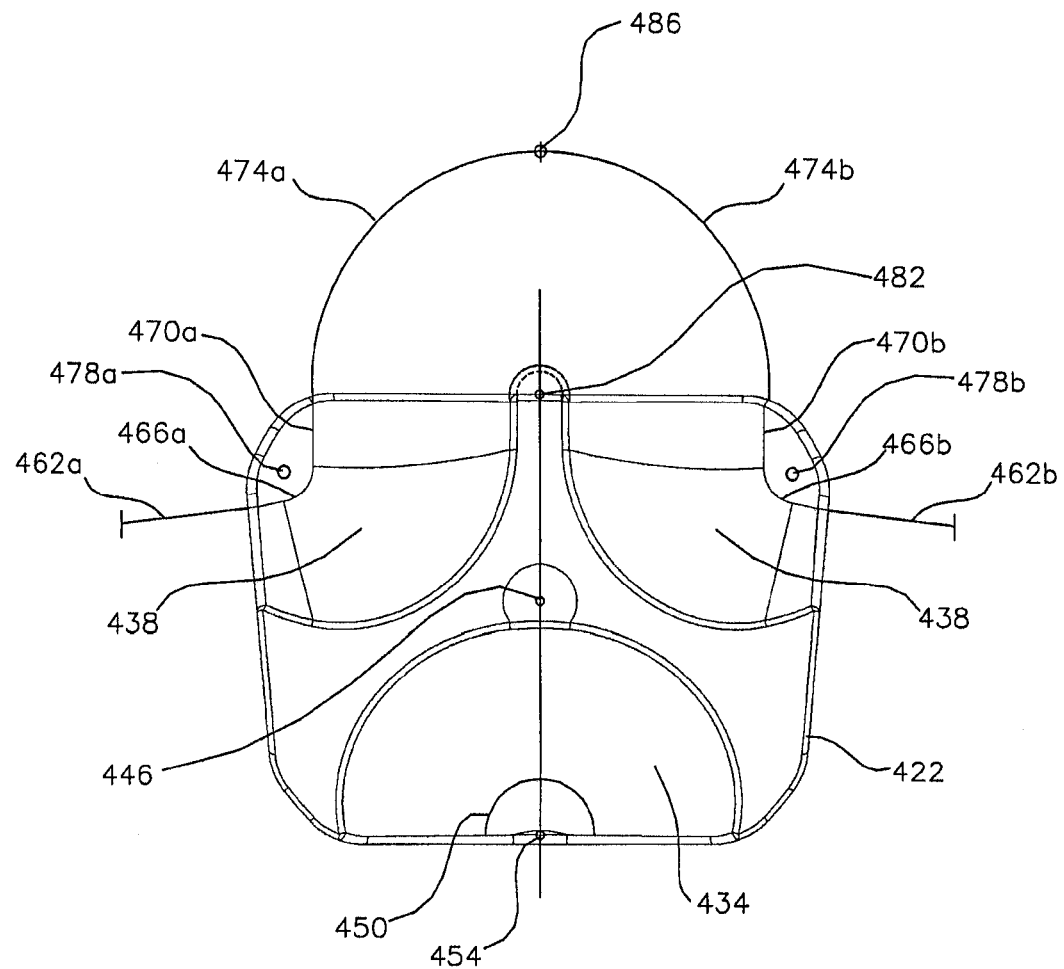
FIG. 67 shows a top view of the lower portion of the joint of FIG. 54 along with the tool path lines for forming the recesses.
Figure 68:
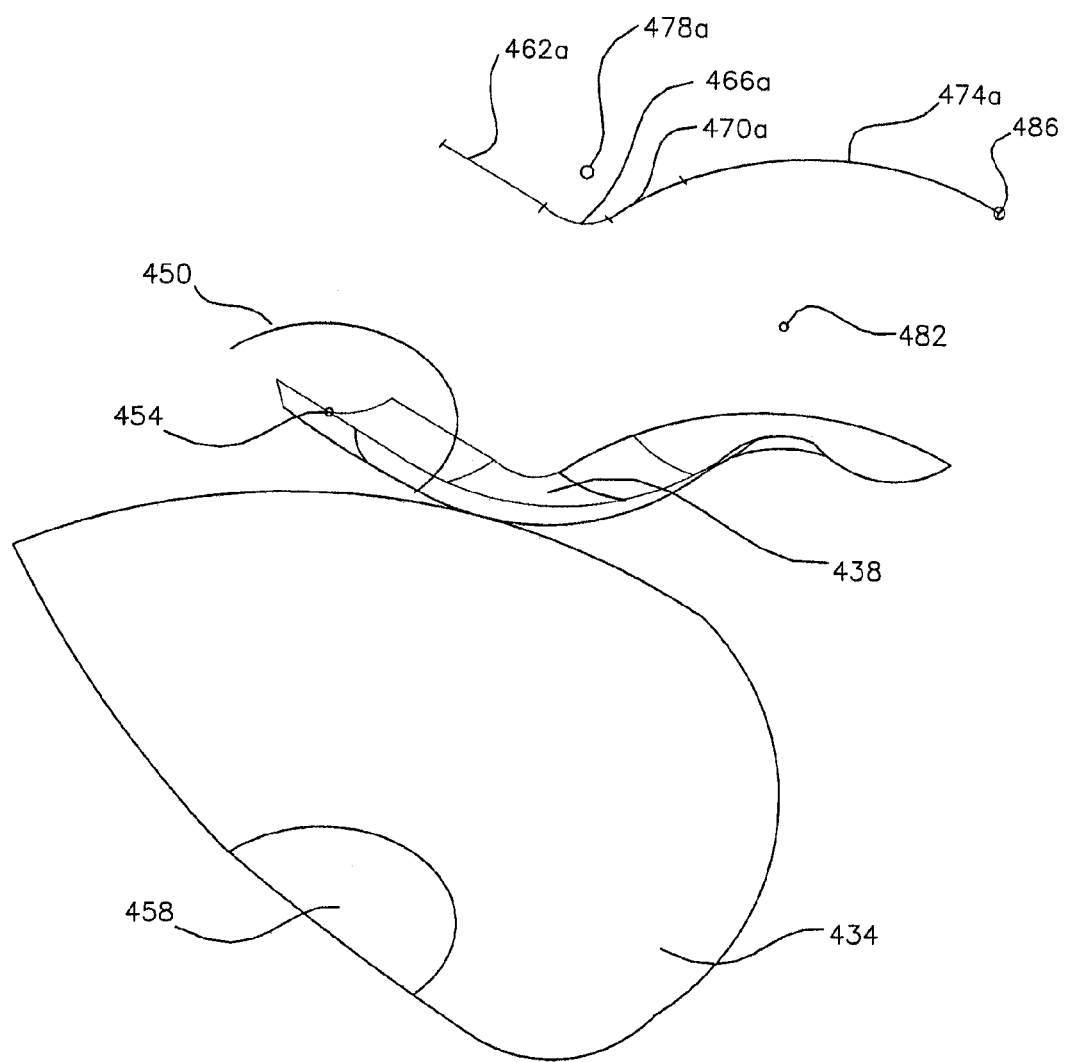
FIG. 68 shows a perspective view of the tool path lines, surfaces formed by the tool and recesses of FIG. 67.

FIGS. 67 and 68 illustrate the grinding/polishing tool paths used to form the lower section 422 as shown. FIG. 67 shows a top view of the tool paths overlaid on the lower portion 422 of the joint, and FIG. 68 shows a perspective view of the tool paths along with the resulting tool cuts and recesses. The posterior recess is made by sweeping a 15 mm diameter circular grinding/polishing tool through a horizontal arc 450 (so that the grinding diameter is perpendicular to the arc) where the arc has approximately a 1.8 mm radius and where the center 454 of the arc is centered laterally on the lower portion 422, positioned 6.4 mm behind central reference point 446 (which is centered laterally and about 5.4 mm from the anterior edge or 6.6 mm from the posterior edge), and so that the center 454 is positioned about 4.9 mm above the upper surface of the lower portion 422. The portion 458 of the posterior recess 434 which is inside of the lowest point ground by the tool is ground flat.

The two lateral anterior recesses 438 are made by sweeping a 10.8 mm diameter circular grinding/polishing tool across the tool path identified by path segments 462*a*, 466*a*, 470*a*, 474*a*, 474*b*, 470*b*, 466*b*, and 462*b*. Tool path segments 462*a*, 462*b* are straight lines of about 3.5 mm length. Tool path segments 466*a*, 466*b* are arcs having centers 478*a*, 478*b* and radii of about 0.9 mm. Tool path segments 470*a*, 470*b* are straight lines about 1.7 mm in length. Tool path segments 474*a*, 474*b* are arcs having a common center 482 and radii of about 6 mm. Center points 478*a*, 478*b* are located about 7 mm to each side of the lateral center line and are located about 4 mm forward of the reference point 446, placing the points about 10.6 mm forward of the center point 454 and about 1.4 mm back from the anterior edge of the lower portion 422. Center point 482 is located along the lateral center line and about 5.9 mm forwards of the reference point 446, or about 0.3 mm forwards of the anterior edge of the lower portion 422.

Figure 64:
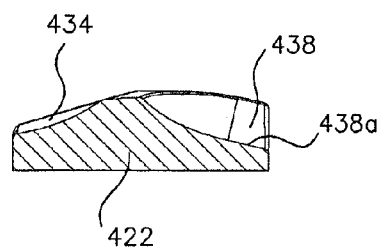

The various tool path segments 462 through 474 are connected into a continuous path as shown, and are located in a single plane. The plane in which the tool path segments are located is angled with respect to the lower segment so as to angle the forward portion 438*a* of the anterior recesses 438 as shown in FIG. 64. As discussed previously, this causes the anterior end of the upper portion 418 to lower slightly relative to the anterior end of the lower portion 422 during flexion of the spine, replicating the natural motion of the spine. For the embodiment shown in FIGS. 54 through 68, the plane is sloped downwardly about 17 degrees towards the anterior side of the joint. As such, the anterior most point 486 of the tool path (path segments 462 through 474) is located about 0.9 mm above the upper surface of the lower portion 422, and the path segments 470*a*, 470*b* are located about 3.5 mm above the upper surface of the lower portion.

It will be appreciated that the slope of the plane in which the tool path segments 462 through 474 are located may be zero if a simplified manufacturing process is desired. When the plane of the tool path segments 462 through 474 is sloped, it may typically be adjusted to match the specific disc which is being replaced, and may often be sloped at an angle of between about 7 and about 27 degrees less than horizontal. As discussed above, a middle cervical artificial disc will have a slope of about 17 degrees. The slope of the plane will typically be changed by adjusting the height of the anterior most point 486 of the tool path so as to keep the anterior recesses 438 at a similar average height and keep the height of the upper portion 418 relative to the lower portion 422 at a similar distance when the upper portion is in a neutral position.

The artificial spinal joints herein are beneficial in that they provide motion which closely replicates the artificial motion of the spine. An important aspect of this is providing a coupled motion, where translation or rotation of the upper portion relative to the lower portion necessarily produces a tilting of the upper portion relative to the lower portion. While some prior art artificial spine joints allow for translation, and allow for pivoting of the joint in a ball and socket like manner, there is no coupling of the translational movement and pivoting movement which approximates the natural motion of the spine. This results in a joint that provides an unnatural motion when implanted in a spine, and which adversely affects the spine as described herein. To the contrary, the inventive artificial spine joints provide a motion that closely replicates the natural spinal motion.

It is appreciated that the artificial discs disclosed herein will result in a high contact pressure between the projections and the recesses, as the curved surfaces of the projections contact the recesses at a very small contact area. Thus, the material used to create such a projection must withstand a very high pressure without deformation and without the wearing away, breaking, or other degradation of the material. Thus, a preferred embodiment of the present invention provides artificial discs which are formed from diamond, such as polycrystalline diamond compact (PDC). PDC is a sufficiently hard material to resist wear and deformation.

U.S. Publication No. 2003/0191533, assigned to Diamicron, Inc., discusses the manufacture of artificial joints using diamond, and is incorporated herein by reference. The publication makes known to one of skill in the art how to make artificial joints of artificial diamonds. With respect to the present invention, it is appreciated that it is more difficult to form a diamond artificial disc surface which is a complicated multi-projection or multi-recess surface. It is much simpler to form a simple regular surface such as a sphere or hemispherical receptacle.

A presently preferred method of manufacture of the artificial disc of the present invention uses electrical discharge machining (EDM) to form the joint surfaces. The artificial diamond compound may be pressed into roughly the desired shape. A sink EDM machine may then be fitted with an electrode which is the negative shape of the part being produced. The EDM and custom electrode are then used to burn away the diamond compound and refine the shape of the piece of the artificial joint. The resulting piece may then be polished to a finished surface. It is thus appreciated that the difficulty of forming the artificial disc out of diamond is a difficult process and may require some simplification of the artificial disc design.

Another currently preferred method of manufacture of the artificial joint of the present invention uses a circularly shaped grinding and polishing tool to sweep across the recesses and form the curved contact surfaces therein, and used a cup shaped grinding and polishing tool to form the spherical projections on the lower surfaces. This is particularly advantageous in forming the more geometrically shaped contact surfaces of the artificial joints of FIGS. 31 through 66.

While PDC or other diamond materials are preferred, other biologically compatible metals and ceramics may also be used. Those familiar with the construction of artificial joints will be familiar with numerous such materials and the relative advantages and drawbacks of each.

There is thus disclosed an improved artificial vertebral disc. It will be appreciated that numerous changes may be made to the present invention without departing from the scope and spirit of the invention. The appended claims are intended to cover such modifications.

What is claimed is:

1. An artificial disc for forming an artificial joint in a spine comprising:
    an upper portion and a lower portion, the upper portion and lower portion collectively having a plurality of lobes and a plurality of troughs, the lobes engaging the troughs at three contact points disposed in a triangular arrangement with a first contact point which is centered laterally and a second contact point and third contact point which are spaced apart laterally from each other and which are spaced apart from the first contact point in an anterior-posterior direction, wherein the lobes slide across the surfaces of the troughs to different locations within the troughs while remaining in contact with the troughs in order to thereby allow for articulation of the artificial disc.

2. The artificial disc of claim 1, wherein movement of the upper portion in a first direction causes tilting of the upper portion in that direction.

3. The artificial disc of claim 1, wherein the first contact point is defined by contact between a first lobe and a first trough, and wherein the trough comprises a generally horizontal portion disposed away from a center of the artificial disc and wherein the trough transitions from the generally horizontal portion to a sloping portion having a greater vertical slope towards the center of the artificial disc.

4. The artificial disc of claim 3, wherein, from a neutral position of the artificial disc, movement of the first lobe away from the center of the artificial disc moves the first lobe generally horizontally and wherein movement of the first lobe towards the center of the artificial disc moves the first lobe horizontally and vertically to increase the distance between the upper portion and the lower portion of the artificial disc.

5. The artificial disc of claim 1, wherein the first contact point, second contact point, and third contact point are defined by contact between a first lobe, a second lobe, and a third lobe and corresponding articulation surfaces on troughs, and wherein each of the first lobe, second lobe, and third lobe contacts a trough at a location which is curved and a location wherein, from a neutral position of the artificial disc, movement of the lobe along the trough in a first direction is generally horizontal and movement of the lobe along the trough in a second direction opposite the first direction is generally horizontal and vertical.

6. An artificial disc comprising:
    an upper portion having a bone attachment surface on an upper side thereof and an upper articulation surface on a lower side thereof;
    a lower portion having a bone attachment surface on a lower side thereof and a lower articulation surface on an upper side thereof;
    wherein the upper articulation surface and the lower articulation surface comprise a plurality of projections which slide across corresponding recesses, wherein the upper articulation surface contacts the lower articulation surface at three locations, wherein the upper surface moves relative to the lower surface during articulation of the artificial disc such that the upper articulation surface remains in contact with the lower articulation surface at the three locations, and wherein the upper articulation surface and the lower articulation surface comprise a first projection and a corresponding first recess which contact each other, and wherein the recess is curved so that a first section located away from a center of the artificial disc is generally horizontal and so that a second section located closer towards a center of the artificial disc than the first section is horizontal and vertical, wherein the recess transitions smoothly between the first section and the second section, and wherein the first projection moves between the first section and the second section during articulation of the artificial disc.

7. The artificial disc of claim 6, wherein the three locations comprise a first location which is centered laterally and a second location and a third location which are spaced apart laterally from each other and which are spaced apart in an anterior-posterior direction from the first location.

8. The artificial disc of claim 6, wherein the artificial disc comprises three projections which are spaced apart in a triangular arrangement.

9. The artificial disc of claim 8, wherein the three projections are curved and wherein the three projections contact the opposing articulation surface at a location which is curved and which has a greater radius of curvature to allow the projection to move to different locations on the opposing articulation surface during articulation of the artificial disc.

10. An artificial disc comprising:
an upper portion having a bone attachment surface on an upper side thereof and an upper articulation surface on a lower side thereof;
a lower portion having a bone attachment surface on a lower side thereof and a lower articulation surface on an upper side thereof;
wherein the upper articulation surface comprises a plurality of projections and wherein the lower articulation surface comprises a plurality of recesses;
wherein the plurality of projections contact the plurality of recesses at three points; and
wherein the upper articulation surface comprises a first projection of the plurality of projections and wherein the lower articulation surface comprises a first recess of the plurality of recesses which has a generally horizontal section disposed away from a center of the artificial disc and which transitions towards a more vertically sloped sections towards the center of the artificial disc.

11. The artificial disc of claim 10, wherein, in a neutral position of the artificial disc, each projection contacts the lower articulation surface at a location which extends generally horizontally in a first direction and horizontally and vertically in a second direction opposite the first direction.

12. The artificial disc of claim 10, wherein the upper articulation surface comprises three projections, wherein the first projection is centered laterally and wherein second and third projections are spaced apart laterally from each other and spaced apart in an anterior-posterior direction relative to the first projection.

* * * * *